(12) United States Patent
Oronsky et al.

(10) Patent No.: US 10,342,778 B1
(45) Date of Patent: Jul. 9, 2019

(54) TREATMENT OF BRAIN METASTASES USING ORGANONITRO COMPOUND COMBINATION THERAPY

(71) Applicant: EpicentRx, Inc., Mountain View, CA (US)

(72) Inventors: Bryan T. Oronsky, Los Altos Hills, CA (US); Jan Scicinski, Saratoga, CA (US)

(73) Assignee: EpicentRx, Inc., La Jolla, CA (US)

( * ) Notice: Subject to any disclaimer, the term of this patent is extended or adjusted under 35 U.S.C. 154(b) by 163 days.

(21) Appl. No.: 15/298,735

(22) Filed: Oct. 20, 2016

Related U.S. Application Data

(60) Provisional application No. 62/243,761, filed on Oct. 20, 2015.

(51) Int. Cl.
| | | |
|---|---|---|
| *A61N 5/10* | (2006.01) | |
| *A61K 31/397* | (2006.01) | |
| *A61K 9/00* | (2006.01) | |
| *A61K 31/495* | (2006.01) | |

(52) U.S. Cl.
CPC .......... *A61K 31/397* (2013.01); *A61K 9/0019* (2013.01); *A61K 31/495* (2013.01); *A61N 5/10* (2013.01); *A61N 2005/109* (2013.01); *A61N 2005/1087* (2013.01); *A61N 2005/1089* (2013.01)

(58) Field of Classification Search
CPC ................................ A61K 9/0019; A61N 5/10
See application file for complete search history.

(56) References Cited

U.S. PATENT DOCUMENTS

| | | |
|---|---|---|
| 2,978,453 A | 4/1961 | Milton |
| 3,845,770 A | 11/1974 | Theeuwes et al. |
| 3,916,899 A | 11/1975 | Theeuwes et al. |
| 4,765,539 A | 8/1988 | Noakes et al. |
| 5,112,598 A | 5/1992 | Biesalski |
| 5,336,784 A | 8/1994 | Hiskey et al. |
| 5,521,203 A | 5/1996 | Adams et al. |
| 5,556,611 A | 9/1996 | Biesalski |
| 5,579,458 A | 11/1996 | Yokosuka et al. |
| 5,580,988 A | 12/1996 | Dave |
| 5,693,794 A | 12/1997 | Nielsen |
| 5,698,155 A | 12/1997 | Grosswald et al. |
| 5,950,619 A | 9/1999 | van der Linden et al. |
| 5,954,047 A | 9/1999 | Armer et al. |

(Continued)

FOREIGN PATENT DOCUMENTS

| | | |
|---|---|---|
| DE | 10111049 A1 | 9/2002 |
| EP | 0412211 A1 | 2/1991 |

(Continued)

OTHER PUBLICATIONS

Alderman, D., "A Review of Cellulose Ethers in Hydrophilic Matrices for Oral Controlled-Release Dosage Forms," *Int. J. Pharm. Tech. & Prod. Mfr.*, 1984, vol. 5, No. 3, pp. 1-9.

(Continued)

*Primary Examiner* — Christine H Matthews
(74) *Attorney, Agent, or Firm* — Goodwin Procter LLP

(57) ABSTRACT

The invention provides therapeutic methods and kits for treating brain metastases using a particular dosing regimen of the organonitro compound ABDNAZ, radiation therapy, and optionally an additional anti-cancer agent.

30 Claims, 1 Drawing Sheet

Hours Between Administration of ABDNAZ and Radiation Therapy

(56) References Cited

U.S. PATENT DOCUMENTS

| | | | |
|---|---|---|---|
| 5,970,974 | A | 10/1999 | Van Der Linden et al. |
| 6,133,320 | A | 10/2000 | Yallampalli et al. |
| 6,245,799 | B1 | 6/2001 | Asselin et al. |
| 6,391,911 | B1 | 5/2002 | Bases |
| 6,407,236 | B1 | 6/2002 | Baraldi et al. |
| 7,163,958 | B2 | 1/2007 | Earl et al. |
| 7,507,842 | B2 | 3/2009 | Oehler et al. |
| 7,745,643 | B2 | 6/2010 | Cannizzo et al. |
| 8,178,698 | B2 | 5/2012 | Cannizzo et al. |
| 8,299,053 | B2 | 10/2012 | Bednarski et al. |
| 8,664,247 | B2 | 3/2014 | Scicinski et al. |
| 8,927,527 | B2 | 1/2015 | Bednarski et al. |
| 9,139,519 | B2 | 9/2015 | Scicinski et al. |
| 9,226,915 | B2 | 1/2016 | Bednarski et al. |
| 9,468,625 | B2 | 10/2016 | Scicinski et al. |
| 9,987,270 | B1 * | 6/2018 | Oronsky ............. A61K 31/495 |
| 2002/0137770 | A1 | 9/2002 | Nara et al. |
| 2004/0024057 | A1 | 2/2004 | Earl et al. |
| 2004/0167212 | A1 | 8/2004 | Bednarski et al. |
| 2006/0111272 | A1 | 5/2006 | Roberts et al. |
| 2007/0135384 | A1 | 6/2007 | Bednarski et al. |
| 2008/0255149 | A1 | 10/2008 | Dobler et al. |
| 2008/0256149 | A1 | 10/2008 | Bansal et al. |
| 2009/0093644 | A1 | 4/2009 | Cannizzo et al. |
| 2009/0163466 | A1 | 6/2009 | Bednarski et al. |
| 2011/0130572 | A1 | 6/2011 | Cannizzo et al. |
| 2011/0195947 | A1 | 8/2011 | Straessler et al. |
| 2012/0149678 | A1 | 6/2012 | Oronsky et al. |
| 2013/0123216 | A1 | 5/2013 | Bednarski et al. |
| 2014/0308260 | A1 | 10/2014 | Oronsky et al. |
| 2015/0246020 | A1 | 9/2015 | Bednarski et al. |
| 2016/0081981 | A1 | 3/2016 | Scicinski et al. |
| 2016/0199346 | A1 | 7/2016 | Bednarski et al. |

FOREIGN PATENT DOCUMENTS

| | | |
|---|---|---|
| WO | WO-95/32715 A1 | 12/1995 |
| WO | WO-96/36602 A1 | 11/1996 |
| WO | WO-98/16485 A1 | 4/1998 |
| WO | WO-99/16436 A1 | 4/1999 |
| WO | WO-99/59575 A1 | 11/1999 |
| WO | WO-00/06143 A1 | 2/2000 |
| WO | WO-01/077100 A2 | 10/2001 |
| WO | WO-04/032864 A2 | 4/2004 |
| WO | WO-04/098538 A2 | 11/2004 |
| WO | WO-04/113281 A1 | 12/2004 |
| WO | WO-05/046661 A2 | 5/2005 |
| WO | WO-2007/022121 A2 | 2/2007 |
| WO | WO-2007/022225 A2 | 2/2007 |

OTHER PUBLICATIONS

Ansari et al., "Primary squamous cell carcinoma of the prostate: a rare clinicopathological entity. Report of 2 cases and review of literature," *Urol. Int.*, 2001, vol. 66, No. 4, pp. 216-219 (abstract).
Archibald et al., "Synthesis and X-ray Crystal Structure of 1,3,3-Trinitroazetidine," *J. Org. Chem.*, 1990, vol. 55, pp. 2920-2924.
Bamba et al., "Release Mechanisms in Gelforming Sustained Release Preparations," *Int. J. Pharm.*, 1979, vol. 2, pp. 307-315.
Dave, P., "Acylative Dealkylation of N-tert-Butyl-3-substituted Azetidines: Facile Access to [1.1.0] Azabicyclobutane, 3-Hydroxyazetidinium Hydrochloride, and 3-Azetidinones," *J. Org. Chem.*, 1996, vol. 61, pp. 5453-5455.
During et at,"Controlled Release of Dopamine from a Polymeric Brain Implant: In Vivo Characterization," *Annals of Neurology*, 1989, vol. 25, No. 4, pp. 351-356.
Electrochemical Oxidation of Alkylnitro Compounds PP-1345, A SERDP 'SEED' Activity, initial submission Jun. 30, 2004; amended Aug. 17, 2004; points of contact Scott K. Lusk and Alan N. Green.
Granelli, P. "SEL 1L and Squamous Cell Carcinoma of the Esophagus," *Clinical Cancer Research*, 2004, vol. 10, pp. 5857-5861.
Hiskey et al., "Preparation of 1-Substituted-3,3-Dinitroazetidines," *Journal of Energetic Materials*, 1999, vol. 17, pp. 233-254.

Hockel et al.,"Tumor Hypoxia: Definitions and Current Clinical, Biologic, and Molecular Aspects," *Journal of the National Cancer Institute*, 2001, vol. 93, No. 4, pp. 266-276.
Howard et al., "Intracerebral Drug Delivery in Rats with Lesion-Induced Memory Deficits," *J. Neurosurg.*, 1989, vol. 71, pp. 105-112.
International Search Report for PCT/US2006/031917 dated Jul. 20, 2007.
International Search Report for PCT/US2011/021500 dated May 3, 2011.
Kornblum et al., "Oxidative Substitution of Nitroparaffin Salts," *J. Org. Chem.*, 1983, vol. 48, pp. 332-337.
Langer et al.,"Chemical and Physical Structure of Polymers as Carriers for Controlled Release of Bioactive Agents: A Review, " *JMS-Rev. Macromol. Chem. Phys.*, 1983, Ch. 23, pp. 61-126.
Langer, R., "New Methods of Drug Delivery," *Science* (1990) vol. 249, No. 4976, pp. 1527-1533.
Levy, R., et al. "Inhibition of Calcification of Bioprosthetic Heart Valves by Local Controlled-Release Diphosphonate," *Science* (1985) vol. 228, No. 4696, pp. 190-192.
Ling et al., "Phase I study of CM-Na combined with concurrent radiochemotherapy for advanced esophageal carcinoma," *Chinese Journal of Cancer*, 2005, vol. 24, No. 5, (abstract).
Lopez-Ferrer et al., "Differences in the O-Glycosylation Patterns Between Lung Squamous Cell Carcinoma and Adenocarcinoma," *Am. J. Clin. Pathol.*, 2002, vol. 118, pp. 749-755.
Maxwell et al., "Hypoxia-inducible factor-1 modulates gene expression in solid tumors and influences both angiogenesis and tumor growth," *Proc. Natl. Acad. Sci. USA*, 1997, vol. 94, pp. 8104-8109.
Sauder, C. "A Preliminary Trial of the Programmable Implantable Medication System for Insulin Delivery," *The New England Journal of Medicine*, 1989, vol. 321, No. 9, pp. 574-579.
Sefton, M., "Implantable Pumps," *CRC Crit. Rev. Biomed. Eng.*, 1987, vol. 14, No. 3, pp. 201-237.
Shokeir, A., "Squamous Cell Carcinoma of the Bladder: pathology, diagnosis and treatment," *BJU International*, 2004, vol. 93, pp. 216-220.
Stratford et al.,"Bioreductive drugs into the next millennium," *Anti-Cancer Drug Design*, 1998, vol. 13, pp. 519-528.
Verma et al., "Osmotically Controlled Oral Drug Delivery," *Drug Dev. Ind. Pharm.*, 2000, vol. 26, No. 7, pp. 695-708.
Wilson,et al., "Radiation-activated prodrugs as hypoxia-selective cytotoxins: model studies with nitroarylmethyl quaternary salts," *Anti-Cancer Drug Design*, 1998, vol. 13, pp. 663-685.
Written Opinion of the International Searching Authority for PCT/US2006/031722 dated May 29, 2007.
Written Opinion of the International Searching Authority for PCT/US2006/031917 dated Jul. 20, 2007.
Written Opinion of the International Searching Authority for PCT/US2011/021500 dated May, 2011.
Yen et al., "$^{18}$F-FDG Uptake in Squamous Cell Carcinoma of the Cervix is Correlated with Glucose Transporter 1 Expression," *The Journal of Nuclear Medicine*, 2004, vol. 45, No. 1, pp. 22-29.
Raleigh et al. "Pharmacokinetics of Isotretinoin (ISO) in Rats Following Oral Dosing or Aerosol Inhalation," *British J. Cancer*, 1999, vol. 80, Suppl. 2, 96, p. 269.
Australian Examination Report No. 2 on patent application No. 2006279589, dated May 18, 2012.
Dave, P.R. et al., "Convenient Acylative Dealkylation of Tertiary Amines," *Journal of Organic Chemistry*, 2000, vol. 65, pp. 1207-1209.
Feuer et al., "The Mannich reaction of certain dinitro alcohols with glycine and ethanolamine," *Journal of American Chemical Society*, 1954, vol. 76, pp. 5124-5126.
Marchand, A. P. et al.," Additions of X-Y Across the C(3)-N σ-Bond in 1-Aza-3-ethylbicyclo[1.1.0]butane, Novel Routes to 3-Substituted Azetidines," *Journal of Organic Chemistry*, 1994, vol. 59, No. 18, pp. 5499-5501.
McKenney et al., "Synthesis and thermal properties of 1,3-dinitro-3-(1', 3'-dinitroazetidin-3'-yl)azetidine (TNDAZ) and its admixtures with 1,3,3-trinitroazetidine (TNAZ)," *Journal of Energetic Materials*, 1998, vol. 16, pp. 199-235.

(56) References Cited

OTHER PUBLICATIONS

Oxley J. et al., "Thermal Decomposition Pathways of 1,3,3-Trinitroazetidine (TNAZ), Related 3,3-Dinitroazetidium Salts, and 15N, 13C, and 2H Isotopomers," *Journal of Physical Chemistry A*, 1997, vol. 101, No. 24, pp. 4375-4383.
Padwa et al., "Diastereofacial selectivity in azomethine ylide cycloaddition reactions derived from chiral o-cyanoaminosilanes," *Tetrahedron* (1985) vol. 41, No. 17, pp. 3529-3535.
Peiris, S. M. et al., "Structures of dinitroazetidine and three of its carbonyl derivatives," *Journal of Chemical Crystallography*, 2001, vol. 30, No. 10, pp. 647-653.
Sikder et al., "1,3,3-Trinitroazetidine (TNAZ), a melt-cast explosive: synthesis, characterization and thermal behavior," *Journal of Hazardous Materials*, vol. 113, 2004, pp. 35-43.
Yarmukhamedov et al., "One-step synthesis of substituted 3,5-dinitropiperidines and 1,5-dinitro-3,7-diazabicyclo(3.3.1)nonanes from 1,3-dinitropropanes," *Russian Chemical Bulletin, International Edition*, 2005, vol. 54, No. 2, pp. 414-420.
Crowder et al., (1999) "Vibrational analysis of high-energy compounds: 1,3,3-trinitroazetidine and 1-acetyl-3, 3-dinitroazetidine," *Journal of Energetic Materials*, vol. 17(1), pp. 49-68.
Chawla, Garima, et al., "Challenges in Polymorphism of Pharmaceuticals," CRIPS, vol. 5, No. 1, Jan.-Mar. 2004, pp. 9-12.
Huguenin, Sandra, et al., "Evaluation of the antitumoral potential of different nitric oxide-donating non-steroidal anti-inflammatory drugs (NO-NSAIDs) on human urological tumor cell lines," *Cancer Letters* (2005) vol. 218, pp. 163-170.
Naimi, Ebrahim, et al., "Synthesis of 3'- and 5'-Nitrooxy Pyrimidine Nucleoside Nitrate Esters: "Nitric Oxide Donor" Agents for Evaluation as Anticancer and Antiviral Agents," *J. Med. Chem.* (2003) vol. 46, pp. 995-1004.
Newman, Ann W. and Byrn, Stephen R. "Solid-state analysis of the active pharmaceutical ingredient in drug products," *Drug Discovery Today* (2003) vol. 8, No. 19, pp. 898-905.
Langer, Robert S., et al., eds., "Medical Applications of Controlled Release," vol. 1, Classes of Systems, Ch. 2, pp. 42-67, CRC Press, Inc., Boca Raton, FL, copyright 1984.
Remington, "The Science and Practice of Pharmacy," 19th Edition, vol. II, pp. 1495-1562, 1577-1614, and 1660-1692; Mack Publishing Company, Easton, PA, 1995.
Rosenthal, David I., "A Phase I Single-Dose Trial of Gadolinium Texaphyrin (Gd-Tex), a Tumor Selective Radiation Sensitizer Detectable by Magnetic Resonance Imaging," *Clinical Cancer Research* (1999) vol. 5, No. 4, pp. 739-745.
Smolen, Victor F., et al., eds., "Controlled Drug Bioavailability," vol. 1, Drug Product Design and Performance, Ch. 7, pp. 203-237, John Wiley & Sons, New York, NY, copyright 1984.
Treat, Joseph, et al., "Liposome Encapsulated Doxorubicin: Preliminary Results of Phase I and Phase II Trials," pp. 353-365 of "Liposomes in the Therapy of Infectious Diseases and Cancer, Proceedings of the Ciba-Geigy-Squibb-UCLA Colloquium at Lake Tahoe, CA, Feb.16-20, 1988," Lopez-Berestein, G. and Fidler, I. J. (eds.), Alan R. Liss, Inc., New York, 1989.
Goodson, J. Max, "Dental Applications," Chapter 6 of Medical Applications of Controlled Release, vol. II, pp. 115-138, CRC Press, Inc., Boca Raton, FL, copyright 1984.
Jia, Q., et al., "NO donors with anticancer activity," *Expert Opin. Therapeut. Patents* (2002) vol. 12, No. 6, pp. 819-826.
Konovalova, N.P., et al., "Nitric oxide donor increases the efficiency of cytostatic therapy and retards the development of drug resistance," *Nitric Oxide* (2003) vol. 8, No. 1, pp. 59-64.
Sandler, G., "Clinical evaluation of propatylnitrate in angina pectoris," *British Medical Journal*, vol. 2, No. 5269 (Dec. 30, 1961), pp. 1741-1744.
Stamler, J.S., et al., "Inhaled ethyl nitrite gas for persistent pulmonary hypertension in infants," *The Lancet* (2002) vol. 360, No. 9350, p. 2077.
International Search Report for PCT/US2006/031722 dated May 29, 2007.
Nitrates and Nitrites Answers to Frequently Asked Questions, Ohio Bureau of Environmental Health, Health Assessment Section, Nov. 1, 2006. (2 pages).
Johnson, J.. et al., "Relationships Between Drug Activity in NCI Preclinical in Vitro and in Vivo Models and Early Clinical Trials," *British J. Cancer* (2001) vol. 84, No. 10, pp. 1424-1431.
Kashfi, Khosrow, et al., "Nitric Oxide-Donating Nonsteroidal Anti-Inflammatory Drugs Inhibit the Growth of Various Cultured Human Cancel Cells: Evidence of a Tissue Type-Independent Effect," *J. Pharmacology Experimental Therapeutics* (2002) vol. 303, No. 3, pp. 1273-1282.
Mendenhall, William M., et al., "Radiation Therapy for Squamous Cell Carcinoma of the Tonsillar Region: A Preferred Alternative to Surgery?" *J. Clinical Oncology* (2000) vol. 18, No. 11, pp. 2219-2225.
Sausville, Edward A., et al., "Contributions of Human Tumor Xenografts to Anticancer Development," *Cancer Research* (2006) vol. 66, No. 7, pp. 3351-3354.
Morales-Suarez-Varela, Maria M., et al., "Impact of Nitrates in Drinking Water on Cancer Mortality in Valencia, Spain," European Journal of Epidemiology, 1995, pp. 15-21, vol. 11.
Prezioso, J.A., et al., Genetic Toxicity Evaluation of 1, 3, 3-Trinitroazetidine, vol. IV: Summary Report on the Genotoxicity of TNAZ, AL/OE-TR-1994-0069 vol. IV of IV, Oct. 1994, 22 pages, Air Force Materiel Command, Wright-Patterson Air Force Base, Ohio.
Simpson, R.L., et al., Characterization of TNAZ, UCRL-ID-119672, Dec. 14, 1994, Lawrence Livermore National Laboratory, 15 pages.
Watt, Duncan S. and Cliff, Matthew D. "Evaluation of 1,3,3-Trinitrozaetidine (TNAZ)—A High Performance Melt-Castable Explosive," Weapons Systems Division, Aeronautical and Maritime Research Laboratory, Melbourne, Australia. Report No. DSTO-TR-1000, Issue date Jul. 2000. (34 pages).
Watt, Duncan S. and Cliff, Matthew D. "TNAZ Based Melt-Cast Explosives: Technology Review and AMRL Research Directions," Weapons Systems Division, Aeronautical and Maritime Research Laboratory, Melbourne, Australia. Report DSTO-TR-0702, Issue date Jul. 1998. (37 pages).
West, Anthony R., Solid State Chemistry and its Applications, 1988, pp. 358, and 365, Wiley, New York.
Akhavan, Jacqueline, Explosives and Propellants, Kirk-Othmer Encyclopedia of Chemical Technology, Sep. 17, 2004, pp. 719-744.
Muehlstaedt et al., CAPLUS, 1976:89768, Copyright 2008. (1 page).
Crowder et al., caplus an 1999: 171384.
Hiskey et al., caplus an 1993:233785.
Hiskey et al., caplus an 1994:700750.
Zhang et al, caplus an 1998:460439.
International Search Report and Written Opinion for PCT/US2011/064178 dated Apr. 17, 2012. (8 pages).
International Search Report and Written Opinion for PCT/US2012/038592 dated Aug. 10, 2012. (11 pages).
Coburn et al., caplus an 1998:567551.
Garver et al., "Catalyzed Oxidative Nitration of Nitronate Salts," *J. Org. Chem.* 1985, vol. 50, No. 10, pp. 1699-1702.
Hiskey et al., caplus an 1999:411860.
Katritzky et al.,"Novel Syntheses of 1,3,3-Trinitroazetidine," *J. Heterocyclic Chem.*, Mar.-Apr. 1994, vol. 31, pp. 271-275.
Marchand et al., "A Novel Approach to the Synthesis of 1,3,3-Trinitroazetidine," *J. Org Chem.* 1995, vol. 60, No. 15, pp. 4943-4946.
Nara et al., caplus an 2002:169585; 2002.
Straessler et al., "Development of a Safe and Efficient Two-Step Synthesis for Preparing 1-Bromoacetyl-3,3-dinitroazetidine, a Novel Clinical Anticancer Candidate," *Organic Process Research & Development*, 2012, vol. 16, pp. 512-517.
TEMODAR Prescribing Information (year 2008).
"Phase 1 Two Part Dose Escalation Trial of RRx-001 + Radiation + Temozolomide and RRx-001 + Temozolomide Post-RT in Newly Diagnosed Glioblastoma and Anaplastic Gliomas (G-FORCE-1)" from Clinicaltrials.gov, dated Oct. 24, 2016.

(56) References Cited

OTHER PUBLICATIONS

"Dose-Escalation Study of RRx-001 in Combination With Whole Brain Radiation in Subjects With Brain Metastases (BRAIN-STORM)" from Clinicaltrials.gov.

Ning, S. et al., "Dinitroazetidines Are a Novel class of Anticancer Agents and Hypoxia-Activated Radiation Sensitizers Developed from Highly Energetic Materials," *Cancer Res.* (2012) vol. 72, pp. 2600-2608.

Oronsky, B. T. et al., "A Review of Two Promising Radiosensitizers in Brain Metastases: Rrx-001 and 2-Deoxyglucose," *J. Cancer Sci. Ther.* (2015) vol. 7, pp. 137-141.

U.S. Appl. No. 15/337,378, Treatment of Gliomas Using Organonitro Compound Combination Therapy, filed Oct. 28, 2016.

* cited by examiner

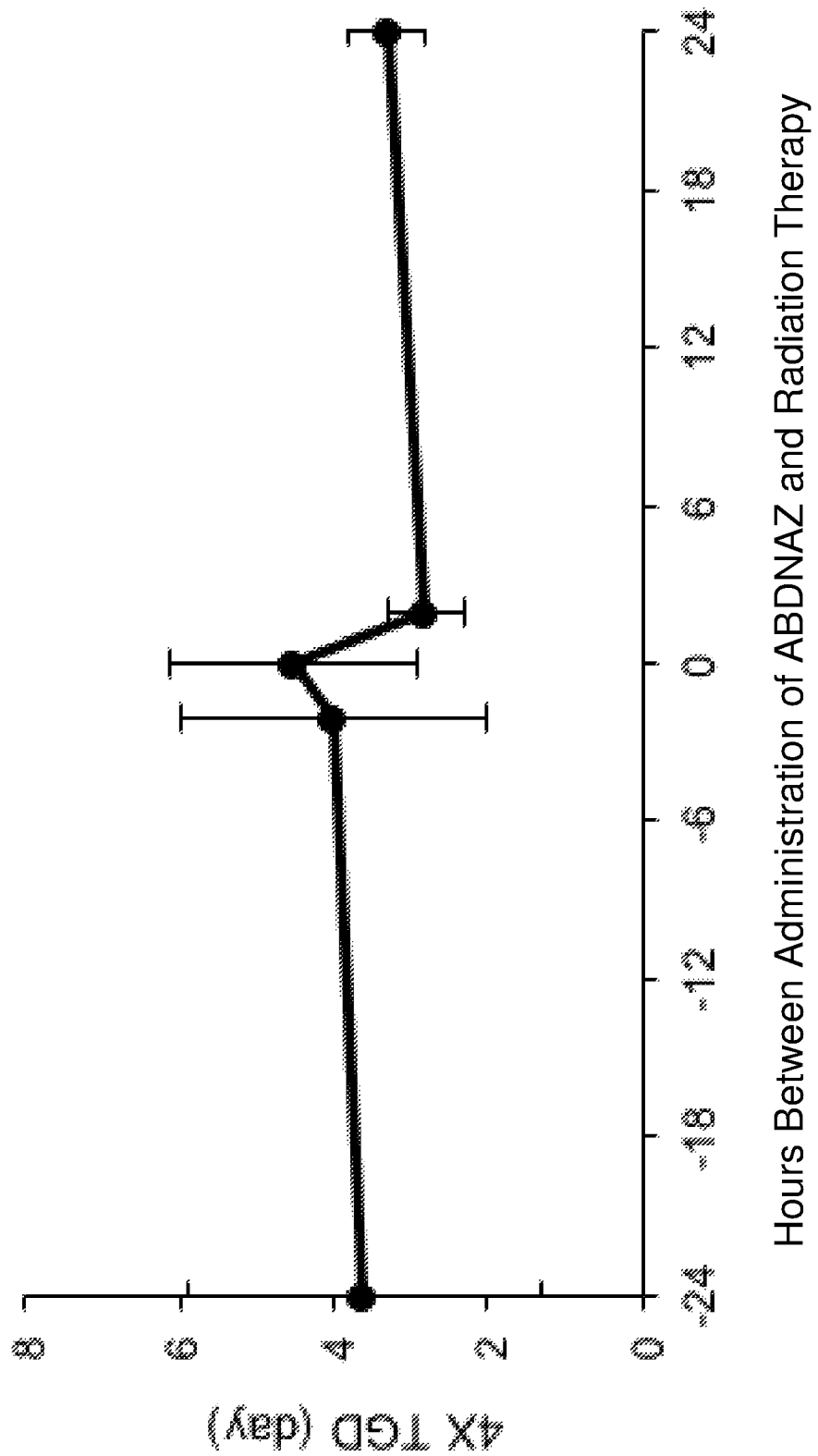

TREATMENT OF BRAIN METASTASES USING ORGANONITRO COMPOUND COMBINATION THERAPY

CROSS REFERENCE TO RELATED APPLICATION

This application claims the benefit of and priority to U.S. Provisional Patent Application Ser. No. 62/243,761 filed Oct. 20, 2015, the contents of which are hereby incorporated by reference.

FIELD OF THE INVENTION

The invention provides therapeutic methods and kits for treating brain metastases using a particular dosing regimen of the organonitro compound ABDNAZ, radiation therapy, and optionally an additional anti-cancer agent.

BACKGROUND

Brain metastases are a frequent intracranial neoplasm in adults. Estimates of the incidence of brain metastases in the United States range between 100,000 to 200,000 patients annually, representing a major oncologic problem. Recent estimates also suggest that the frequency of brain metastases is rising due to patients living longer after primary cancer diagnosis. This is believed to a result of earlier diagnosis and more effective treatments for the primary cancer. While brain metastases can result from various types of primary cancer, brain metastases are more frequently observed in patients that have melanoma or a cancer of the lung, breast, colon, or kidney.

The standard of care for patients with 1-3 brain metastases otherwise eligible for local therapy is typically surgery or stereotactic radiosurgery, with or without adjuvant whole brain radiation therapy (WBRT). In patients with 4 or more brain metastases, the standard of care is generally whole brain radiation therapy for improved intracranial disease control and neurologic outcome. In these patients, external beam radiation therapy remains an important treatment in slowing the progression of intracranial disease.

However, even using the current standards of care for treating brain metastases, survival outcomes remain poor. For example, survival outcomes often average 4-6 months in patients suffering from brain metastases even upon receiving the current standard of care. The magnitude of the number of patients diagnosed annually with a brain metastasis, coupled with the poor survival outcome highlights the urgent need for new treatment options for patients suffering from a brain metastasis.

The present invention addresses this need for improved treatment regimens for patients suffering from a brain metastasis and provides other related advantages.

SUMMARY

The invention provides therapeutic methods and kits for treating brain metastases using a particular dosing regimen of the organonitro compound ABDNAZ, radiation therapy, and optionally an additional anti-cancer agent. The compound ABDNAZ has the following chemical structure:

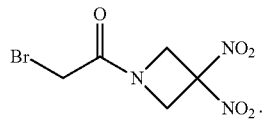

The therapeutic methods and kits provide a solution to the long unmet need for a more effective treatment for patients suffering from a brain metastasis, such as a brain metastasis arising from a melanoma, lung cancer, breast cancer, colon cancer, or kidney cancer. The therapeutic method generally entails administering a dose of a therapeutically effective amount of a formulation comprising ABDNAZ to the patient, then subjecting the brain metastasis to a dose of radiation therapy within, for example, twenty-four hours following administration of the dose of the therapeutically effective amount of a formulation comprising ABDNAZ. In preferred embodiments, a dose of a therapeutically effective amount of a formulation comprising ABDNAZ is administered to the patient on a day that the patient receives radiation therapy, and such formulation is administered to the patient within six hours prior to receiving the radiation therapy so that ABDNAZ and the radiation therapy both exert physiological activity during an overlapping time period. The radiation therapy may be administered to the patient for a select number of days (e.g., at least 2, 4, 6, 8, or 10 days) over a two-week period, or a longer duration of time depending on patient response to the therapy. The invention having been generally described is explained in more detail in the aspects and embodiments below and in the detailed description.

Accordingly, one aspect of the invention provides a method of treating a brain metastasis in a patient. The method comprises the steps of: (a) administering to the patient in need thereof a dose of a therapeutically effective amount of a formulation comprising ABDNAZ; and thereafter (b) subjecting the brain metastasis to a first dose of radiation therapy within 24 hours after completing step (a); wherein the radiation therapy provides from about 1 Gy to about 6 Gy of radiation; to thereby treat the brain metastasis. The patient may be administered multiple doses of a formulation comprising ABDNAZ and may be subjected to multiple doses of radiation therapy. For example, in certain embodiments, a dose of a therapeutically effective amount of a formulation comprising ABDNAZ is administered to the patient at a time in the range of 2 days to 4 days after administering the first dose of radiation therapy; and optionally a dose of a therapeutically effective amount of a formulation comprising ABDNAZ is administered to the patient at a time in the range of 6 days to 8 days after administering the first dose of radiation therapy. In certain embodiments, the brain metastasis is subjected to radiation therapy once per day for at least 4 days within a 7 day period following the first dose of radiation therapy, and optionally starting on the seventh day following the first dose of radiation therapy, the brain metastasis is subjected to radiation therapy once per day for at least 5 days within a 7 day period.

Another more specific aspect of the invention provides a method of treating a brain metastasis in a patient, where the method comprises the steps of: (a) intravenously administering to the patient in need thereof a dose of a therapeutically effective amount of a formulation comprising ABDNAZ, and thereafter on the same day subjecting the brain metastasis to a first dose of radiation therapy, wherein the radiation therapy provides from about 1 Gy to about 4 Gy of radiation; (b) beginning on the day following administration of a first dose of radiation therapy, subjecting the brain metastasis to radiation therapy once per day for four consecutive days; (c) on day 3±1 following administration of the first dose of radiation therapy, intravenously administering to the patient a dose of a therapeutically effective amount of a formulation comprising ABDNAZ prior to administration of radiation therapy on the same day; (d) beginning on day 7±1 following administration of the first dose of radiation therapy, subjecting the brain metastasis to radiation therapy once per day for five consecutive days; (e) on day 7±1 following administration of the first dose of radiation therapy, intravenously administering to the patient a dose of a therapeutically effective amount of a formulation comprising ABDNAZ prior to administration of radiation therapy on the same day; and (f) on day 10±1 following administration of the first dose of radiation therapy, intravenously administering to the patient a dose of a therapeutically effective amount of a formulation comprising ABDNAZ prior to administration of radiation therapy on the same day; to thereby treat the brain metastasis. In certain preferred embodiments, the first dose of radiation therapy provides about 3 Gy of radiation. In certain preferred embodiments, each dose of a formulation comprising ABDNAZ provides from about 1 mg/m$^2$ to about 10 mg/m$^2$ of ABDNAZ. In certain preferred embodiments, when a dose of a formulation comprising ABDNAZ is administered to the patient on the same day as radiation therapy, the dose of a formulation comprising ABDNAZ is administered to the patient within about five hours prior to administration of the radiation therapy.

Another more specific aspect of the invention provides a method of treating a brain metastasis in a patient, where the method comprises the steps of: (a) intravenously administering to the patient in need thereof a dose of a therapeutically effective amount of a formulation comprising ABDNAZ, and thereafter on the same day orally administering temozolomide to the patient and subjecting the brain metastasis to a first dose of radiation therapy, wherein the radiation therapy provides from about 1 Gy to about 4 Gy of radiation; (b) beginning on the day following administration of a first dose of radiation therapy, subjecting the brain metastasis to radiation therapy once per day for at least four days within a 6 day period; (c) beginning on the day following administration of a first dose of radiation therapy, orally administering temozolomide to the patient once per day for 13 consecutive days; (d) on day 7±1 following administration of the first dose of radiation therapy, intravenously administering to the patient a dose of a therapeutically effective amount of a formulation comprising ABDNAZ prior to administration of temozolomide and radiation therapy on the same day; (e) beginning on day 7±1 following administration of the first dose of radiation therapy, subjecting the brain metastasis to radiation therapy once per day for at least five days within a 7 day period; (f) on day 21±1 following administration of the first dose of radiation therapy, intravenously administering to the patient a dose of a therapeutically effective amount of a formulation comprising ABDNAZ; (g) on day 21±1 following administration of the first dose of radiation therapy, orally administering temozolomide to the patient once per day for 7 consecutive days; (h) on day 36±1 following administration of the first dose of radiation therapy, intravenously administering to the patient a dose of a therapeutically effective amount of a formulation comprising ABDNAZ; and (i) on day 36±1 following administration of the first dose of radiation therapy, orally administering temozolomide to the patient once per day for 7 consecutive days; to thereby treat the brain metastasis.

Another aspect of the invention provides a kit for treating a brain metastasis. The kit comprises: (i) a formulation comprising ABDNAZ, and (ii) instructions for treating a brain metastasis according to procedures described herein, such as (a) administering to the patient in need thereof a dose of a therapeutically effective amount of a formulation comprising ABDNAZ, and thereafter (b) subjecting the brain metastasis to a first dose of radiation therapy (e.g., within 24 hours after completing step (a)), wherein the radiation therapy provides from about 1 Gy to about 6 Gy of radiation.

BRIEF DESCRIPTION OF THE FIGURES

FIG. 1 is a graph showing delay in SCCVII tumor volume growth in mice that received treatment with ABDNAZ and radiation therapy administered at different times, as described in Example 3 (where the abbreviation TGD refers to tumor growth delay).

DETAILED DESCRIPTION

The invention provides therapeutic methods and kits for treating brain metastases using a particular dosing regimen of the organonitro compound ABDNAZ, radiation therapy, and optionally an additional anti-cancer agent. The compound ABDNAZ has the following chemical structure:

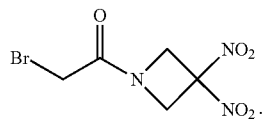

The therapeutic methods and kits provide a solution to the long unmet need for a more effective treatment for patients suffering from a brain metastasis, such as a brain metastasis arising from a melanoma, lung cancer, breast cancer, colon cancer, or kidney cancer. The therapeutic method generally entails administering a dose of a therapeutically effective amount of a formulation comprising ABDNAZ to the patient, then subjecting the brain metastasis to a dose of radiation therapy within, for example, twenty-four hours following administration of the dose of the therapeutically effective amount of a formulation comprising ABDNAZ. In preferred embodiments, a dose of a therapeutically effective amount of a formulation comprising ABDNAZ is administered to the patient on a day that the patient receives radiation therapy, and such formulation is administered to the patient within six hours prior to receiving the radiation therapy so that ABDNAZ and the radiation therapy both exert physiological activity during an overlapping time period. The radiation therapy may be administered to the patient for a select number of days (e.g., at least 2, 4, 6, 8, or 10 days) over a two-week period, or a longer duration of time depending on patient response to the therapy. Various aspects of the invention are set forth below in sections; however, aspects of the invention described in one particular section are not to be limited to any particular section.

I. Therapeutic Methods for Treating Brain Metastases

The invention provides therapeutic methods for treating brain metastases using a particular dosing regimen of the organonitro compound ABDNAZ, radiation therapy, and optionally an additional anti-cancer agent. The therapeutic method generally entails administering a dose of a therapeutically effective amount of a formulation comprising ABDNAZ to the patient, then subjecting the brain metastasis to a dose of radiation therapy within, for example, twenty-four hours following administration of the dose of the therapeutically effective amount of a formulation comprising ABDNAZ. Various features of the methods are described in sections below. The sections are arranged for convenience and information in one section is not limited to that section, but may be applied to other sections.

First Method

One aspect of the invention provides a method of treating a brain metastasis in a patient. The method comprises the steps of: (a) administering to the patient in need thereof a dose of a therapeutically effective amount of a formulation comprising ABDNAZ; and thereafter (b) subjecting the brain metastasis to a first dose of radiation therapy within 24 hours after completing step (a); wherein the radiation therapy provides from about 1 Gy to about 6 Gy of radiation; to thereby treat the brain metastasis.

Second Method

Another more specific aspect of the invention provides a method of treating a brain metastasis in a patient, where the method comprises the steps of: (a) intravenously administering to the patient in need thereof a dose of a therapeutically effective amount of a formulation comprising ABDNAZ, and thereafter on the same day subjecting the brain metastasis to a first dose of radiation therapy, wherein the radiation therapy provides from about 1 Gy to about 4 Gy of radiation; (b) beginning on the day following administration of a first dose of radiation therapy, subjecting the brain metastasis to radiation therapy once per day for four consecutive days; (c) on day 3±1 following administration of the first dose of radiation therapy, intravenously administering to the patient a dose of a therapeutically effective amount of a formulation comprising ABDNAZ prior to administration of radiation therapy on the same day; (d) beginning on day 7±1 following administration of the first dose of radiation therapy, subjecting the brain metastasis to radiation therapy once per day for five consecutive days; (e) on day 7±1 following administration of the first dose of radiation therapy, intravenously administering to the patient a dose of a therapeutically effective amount of a formulation comprising ABDNAZ prior to administration of radiation therapy on the same day; and (f) on day 10±1 following administration of the first dose of radiation therapy, intravenously administering to the patient a dose of a therapeutically effective amount of a formulation comprising ABDNAZ prior to administration of radiation therapy on the same day; to thereby treat the brain metastasis.

Third Method

Another more general aspect of the invention provides a method of treating a brain metastasis in a patient, where the method comprises the steps of: (a) administering to the patient in need thereof a dose of a therapeutically effective amount of a formulation comprising ABDNAZ; and (b) subjecting the brain metastasis to a first dose of radiation therapy.

Fourth Method

Another aspect of the invention provides a method of treating a brain metastasis in a patient. The method comprises the steps of: (a) administering to the patient in need thereof a first dose of a therapeutically effective amount of a formulation comprising ABDNAZ; and thereafter (b) subjecting the brain metastasis to a first dose of radiation therapy at least once within the 7 day period following administration of the first dose of a therapeutically effective amount of a formulation comprising ABDNAZ; wherein the radiation therapy provides from about 1 Gy to about 6 Gy of radiation; to thereby treat the brain metastasis.

Fifth Method

Another more specific aspect of the invention provides a method of treating a brain metastasis in a patient, where the method comprises the steps of: (a) intravenously administering to the patient in need thereof a first dose of a therapeutically effective amount of a formulation comprising ABDNAZ; (b) on day 4±1 following administration of the first dose of ABDNAZ, intravenously administering to the patient a second dose of a therapeutically effective amount of a formulation comprising ABDNAZ and thereafter on the same day subjecting the brain metastasis to a first dose of radiation therapy, wherein the radiation therapy provides from about 1 Gy to about 4 Gy of radiation; (c) beginning on the day following administration of a first dose of radiation therapy, subjecting the brain metastasis to radiation therapy once per day for four consecutive days; (d) on day 3±1 following administration of the second dose of ABDNAZ, intravenously administering to the patient a third dose of a therapeutically effective amount of a formulation comprising ABDNAZ prior to administration of radiation therapy on the same day; (e) beginning on day 7±1 following administration of the second dose of ABDNAZ, subjecting the brain metastasis to radiation therapy once per day for five consecutive days; (f) on day 7±1 following administration of the second dose of ABDNAZ, intravenously administering to the patient a fourth dose of a therapeutically effective amount of a formulation comprising ABDNAZ prior to administration of radiation therapy on the same day; and (g) on day 10±1 following administration of the second dose of ABDNAZ, intravenously administering to the patient a fifth dose of a therapeutically effective amount of a formulation comprising ABDNAZ prior to administration of radiation therapy on the same day; to thereby treat the brain metastasis.

In certain embodiments, the method is more specifically defined as comprising the steps of: (a) intravenously administering to the patient in need thereof a first dose of a therapeutically effective amount of a formulation comprising ABDNAZ; (b) on day 4±1 following administration of the first dose of ABDNAZ, intravenously administering to the patient a second dose of a therapeutically effective amount of a formulation comprising ABDNAZ and within 6 hours thereafter subjecting the brain metastasis to a first dose of radiation therapy, wherein the radiation therapy provides from about 1 Gy to about 4 Gy of radiation; (c) beginning on the day following administration of a first dose of radiation therapy, subjecting the brain metastasis to radiation therapy once per day for four consecutive days; (d) on day 3±1 following administration of the second dose of ABDNAZ, intravenously administering to the patient a third dose of a therapeutically effective amount of a formulation comprising ABDNAZ within 6 hours prior to administration of radiation therapy; (e) beginning on day 7±1 following administration of the second dose of ABDNAZ, subjecting the brain metastasis to radiation therapy once per day for five consecutive days; (f) on day 7±1 following administration of the second dose of ABDNAZ, intravenously administering to the patient a fourth dose of a therapeutically effective amount of a formulation comprising ABDNAZ within 6 hours prior to administration of radiation therapy; and (g) on day 10±1 following administration of the second dose of ABDNAZ, intravenously administering to the patient a fifth dose of a therapeutically effective amount of a formulation comprising ABDNAZ within 6 hours prior to administration of radiation therapy; to thereby treat the brain metastasis.

Sixth Method

Another more specific aspect of the invention provides a method of treating a brain metastasis in a patient, comprising the steps of: (a) intravenously administering to the patient in need thereof a dose of a therapeutically effective amount of a formulation comprising ABDNAZ, and thereafter on the same day orally administering temozolomide to the patient and subjecting the brain metastasis to a first dose of radiation therapy, wherein the radiation therapy provides from about 1 Gy to about 4 Gy of radiation; (b) beginning on the day following administration of a first dose of radiation therapy, subjecting the brain metastasis to radiation therapy once per day for at least four days within a 6 day period; (c) beginning on the day following administration of a first dose of radiation therapy, orally administering temozolomide to the patient once per day for 13 consecutive days; (d) on day 7±1 following administration of the first dose of radiation therapy, intravenously administering to the patient a dose of a therapeutically effective amount of a formulation comprising ABDNAZ prior to administration of temozolomide and radiation therapy on the same day; (e) beginning on day 7±1 following administration of the first dose of radiation therapy, subjecting the brain metastasis to radiation therapy once per day for at least five days within a 7 day period; (f) on day 21±1 following administration of the first dose of radiation therapy, intravenously administering to the patient a dose of a therapeutically effective amount of a formulation comprising ABDNAZ; (g) on day 21±1 following administration of the first dose of radiation therapy, orally administering temozolomide to the patient once per day for 7 consecutive days; (h) on day 36±1 following administration of the first dose of radiation therapy, intravenously administering to the patient a dose of a therapeutically effective amount of a formulation comprising ABDNAZ; and (i) on day 36±1 following administration of the first dose of radiation therapy, orally administering temozolomide to the patient once per day for 7 consecutive days; to thereby treat the brain metastasis.

Exemplary Features of the First, Second, Third, Fourth, and Fifth Methods

The above methods may be further characterized by additional features, such as the timing for administering radiation therapy, and administration of an additional anti-cancer agent.

Timing for Administering Radiation Therapy

The radiation therapy may be administered multiple times, such as multiple times over a defined period of time. Administration of radiation therapy on multiple consecutive days is contemplated to provide therapeutic benefits, such as superior efficacy.

The radiation therapy may be administered on multiple days over a set time period following administration of the first dose of radiation therapy. For example, in certain embodiments, the brain metastasis is subjected to radiation therapy once per day for at least 2 days within a 6 day period following the first dose of radiation therapy. In certain embodiments, the brain metastasis is subjected to radiation therapy once per day for at least 4 days within a 6 day period following the first dose of radiation therapy. In certain embodiments, the brain metastasis is subjected to radiation therapy once per day for two consecutive days following the first dose of radiation therapy. In certain embodiments, the brain metastasis is subjected to radiation therapy once per day for four consecutive days following the first dose of radiation therapy.

The therapeutic method may be further characterized according to the dosing schedule for administering radiation therapy beginning on the day that is seven days after administration of the first dose of radiation therapy. For example, in certain embodiments, starting on the seventh day following the first dose of radiation therapy, the brain metastasis is subjected to radiation therapy once per day for at least 3 days within a 7 day period. In certain embodiments, starting on the seventh day following the first dose of radiation therapy, the brain metastasis is subjected to radiation therapy once per day for at least 5 days within a 7 day period. In certain embodiments, starting on the seventh day following the first dose of radiation therapy, the brain metastasis is subjected to radiation therapy once per day for three consecutive days. In certain embodiments, starting on the seventh day following the first dose of radiation therapy, the brain metastasis is subjected to radiation therapy once per day for five consecutive days.

Additional Anti-Cancer Agent

In certain embodiments, the method further comprises administering an additional anti-cancer agent to the patient. In certain embodiments, the additional anti-cancer agent is temozolomide, cisplatin, carboplatin, trastuzumab, or sunitinib. In yet other embodiments, the additional anti-cancer agent is temozolomide. In certain embodiments, for any day in which temozolomide is administered to the patient, the temozolomide is administered orally at a dosage of from about 75 mg/m$^2$ to about 150 mg/m$^2$.

Further exemplary additional anti-cancer agents include, for example, azacitidine, azathioprine, bleomycin, capecitabine, carmustine, chlorambucil, cyclophosphamide, cytarabine, dacarbazine, daunorubicin, docetaxel, doxifluridine, doxorubicin, epirubicin, epothilone, etoposide, fluorouracil, fulvestrant, gemcitabine, hydroxyurea, idarubicin, imatinib, lomustine, mechlorethamine, mercaptopurine, methotrexate, mitoxantrone, oxaliplatin, paclitaxel, pemetrexed, procarbazine, raloxifene, teniposide, thiotepa, tioguanine, tamoxifen, toremifene, valrubicin, vinblastine, vincristine, vindesine, vinorelbine, and pharmaceutically acceptable salts thereof.

In yet other embodiments, the additional anti-cancer agent is abraxane; acivicin; aclarubicin; acodazole hydrochloride; acronine; adozelesin; aldesleukin; altretamine; ambomycin; ametantrone acetate; amrubicin; amsacrine; anastrozole; anthramycin; asparaginase; asperlin; azacitidine; azetepa; azotomycin; batimastat; benzodepa; bicalutamide; bisantrene hydrochloride; bisnafide dimesylate: bizelesin; bleomycin sulfate; brequinar sodium; bropirimine; busulfan; cactinomycin; calusterone; caracemide; carbetimer; carboplatin; carmustine; carubicin hydrochloride; carzelesin; cedefmgol: celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; de/.aguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatm; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; herceptin; hydroxyurea; idarubicin hydrochloride; ifosfamide; ilmofosine; iproplatin; irinotecan; irinotecan hydrochloride; lanreotide acetate; lapatinib; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; portiromycin; prednimustine; procarbazine hydrochloride; puromycin; puromycin hydrochloride; pyrazofurin; riboprine; romidepsin; safingol; safingol hydrochloride; semustine; simtrazene; sparfosate sodium; sparsomycin; spirogermanium hydrochloride; spiromustine; spiroplatin; a stem cell treatment; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; or zorubicin hydrochloride.

Exemplary Features of the First, Second, Third, Fourth, Fifth and Sixth Methods

The above methods may be further characterized by additional features, such as the dose and other features of the radiation therapy, dose of ABDNAZ administered, type of brain metastasis, and effect of the treatment.

Dose and Other Features of the Radiation Therapy

The dose of radiation described herein for the radiation therapy is contemplated to carefully balance the anti-cancer therapeutic effect with potential adverse side effects associated with exposing a patient to radiation therapy. The amount of radiation used in the radiation therapy may be characterized according to the amount of radiation administered upon a single dose and the amount of radiation administered over a period of time during which multiple doses of radiation are administered.

Accordingly, in certain embodiments, each dose of radiation therapy provides from about 2 Gy to about 4 Gy of radiation. In certain embodiments, each dose of radiation therapy provides about 3 Gy of radiation. In certain other embodiments, each provides from about 1, 2, 3, 4, 5, 6, 7, or 8 Gy of radiation.

In certain embodiments, the radiation therapy provides from about 10 Gy to about 30 Gy of radiation each week for a period of two weeks beginning on the day on which the brain metastasis is subjected to the first dose of radiation therapy. In certain embodiments, the radiation therapy provides from about 10 Gy to about 20 Gy of radiation each week for a period of two weeks beginning on the day on which the brain metastasis is subjected to the first dose of radiation therapy. In certain embodiments, the radiation therapy provides about 15 Gy of radiation each week for a period of two weeks beginning on the day on which the brain metastasis is subjected to the first dose of radiation therapy. In certain embodiments, the radiation therapy provides about 10, 12, 14, 16, 18, 20, 22, 24, 26, 28 or 30 Gy of radiation each week for a period of two weeks beginning on the day on which the brain metastasis is subjected to the first dose of radiation therapy. In certain embodiments, the radiation therapy provides from about 10 Gy to about 12 Gy, about 12 Gy to about 14 Gy, about 14 Gy to about 16 Gy, about 16 Gy to about 18 Gy, about 18 Gy to about 20 Gy, about 20 Gy to about 22 Gy, about 22 Gy to about 24 Gy, about 24 Gy to about 26 Gy, about 26 Gy to about 28 Gy, or about 28 Gy to about 30 Gy of radiation each week for a period of two weeks beginning on the day on which the brain metastasis is subjected to the first dose of radiation therapy.

The radiation therapy can be further characterized according to the scope of tissue exposed to radiation. For example, in certain embodiments, the radiation therapy is whole brain radiation therapy.

The radiation therapy can be further characterized according the radiation therapy technique used to deliver the radiation. For example, in certain embodiments, the radiation therapy is (i) conventional fractionated external beam radiation or (ii) intensity-modulated radiation therapy. In certain embodiments, the radiation therapy is conventional fractionated external beam radiation.

Various types of radiation therapy are used by those skilled in the art and have been described in the literature. Exemplary types of radiation therapy include, for example, radiation therapy comprising gamma rays, X-rays, electron beams, neutron beams, particulate radiation, proton beams, or the like. The source of the radiation is desirably external to the patient, which involves directing a beam of high-energy radiation to the brain metastasis using a machine external to the patient. Desirably the target site (i.e., site of the brain metastasis) is exposed to the radiation therapy for a short duration of time, such as less than about 3 hours, 2 hours, 1 hour, 30 minutes, 15 minutes, 10 minutes, 5 minutes, or 1 minute for each dose of radiation therapy.

Dose of ABDNAZ Administered

The dose ABDNAZ described herein for use in combination with the radiation therapy has been selected in view of the dosing schedule of the radiation therapy and the amount of radiation to be administered to the patient. Unless indicated otherwise, dosing amounts of ABDNAZ are provided according to the number of milligrams of ABDNAZ to be administered to the patient based on the surface area of the patient as measured in $m^2$.

In certain embodiments, the dose ABDNAZ administered to the patient is from about 1 $mg/m^2$ to about 2 $mg/m^2$, about 2 $mg/m^2$ to about 4 $mg/m^2$, about 4 $mg/m^2$ to about 6 $mg/m^2$, about 6 $mg/m^2$ to about 8 $mg/m^2$, about 8 $mg/m^2$ to about 10 $mg/m^2$, about 10 $mg/m^2$ to about 12 $mg/m^2$, about 12 $mg/m^2$ to about 14 $mg/m^2$, about 14 $mg/m^2$ to about 16 $mg/m^2$, about 16 $mg/m^2$ to about 18 $mg/m^2$, about 18 $mg/m^2$ to about 20 $mg/m^2$, about 20 $mg/m^2$ to about 25 $mg/m^2$, about 25 $mg/m^2$ to about 30 $mg/m^2$, about 30 $mg/m^2$ to about 35 $mg/m^2$, about 35 $mg/m^2$ to about 40 $mg/m^2$, about 40 $mg/m^2$ to about 45 $mg/m^2$, about 45 $mg/m^2$ to about 50 $mg/m^2$, about 50 $mg/m^2$ to about 60 $mg/m^2$, or about 60 $mg/m^2$ to about 75 $mg/m^2$.

The dose of ABDNAZ administered to the patient may be further characterized according to both the amount of ABDNAZ and the mode of delivery, such as intravenous infusion. Accordingly, in certain embodiments, each dose of the formulation comprising ABDNAZ is administered to the patient by intravenous infusion providing ABDNAZ in an amount ranging from about 1 $mg/m^2$ to about 90 $mg/m^2$. In certain embodiments, each dose of the formulation comprising ABDNAZ is administered to the patient by intravenous infusion providing ABDNAZ in an amount ranging from about 1 mg/m² to about 10 mg/m². In certain embodiments, each dose of the formulation comprising ABDNAZ is administered to the patient by intravenous infusion providing ABDNAZ in an amount ranging from about 1 mg/m² to about 2.5 mg/m². In certain embodiments, each dose of the formulation comprising ABDNAZ is administered to the patient by intravenous infusion providing ABDNAZ in an amount ranging from about 2.5 mg/m² to about 5 mg/m². In certain embodiments, each dose of the formulation comprising ABDNAZ is administered to the patient by intravenous infusion providing ABDNAZ in an amount ranging from about 5 mg/m² to about 10 mg/m². In certain embodiments, each dose of the formulation comprising ABDNAZ is administered to the patient by intravenous infusion providing ABDNAZ in an amount ranging from about 5 mg/m² to about 7 mg/m². In certain embodiments, each dose of the formulation comprising ABDNAZ is administered to the patient by intravenous infusion providing ABDNAZ in an amount ranging from about 8 mg/m² to about 9 mg/m². In certain embodiments, each dose of the formulation comprising ABDNAZ is administered to the patient by intravenous infusion providing ABDNAZ in an amount ranging from about 10 mg/m² to about 20 mg/m². In certain embodiments, each dose of the formulation comprising ABDNAZ is administered to the patient by intravenous infusion providing ABDNAZ in an amount ranging from about 1 mg/m² to about 1.5 mg/m², about 1.5 mg/m² to about 2 mg/m², about 2 mg/m² to about 2.5 mg/m², about 2.5 mg/m² to about 3 mg/m², about 3 mg/m² to about 3.5 mg/m², about 3.5 mg/m² to about 4 mg/m², about 4 mg/m² to about 4.5 mg/m², about 4.5 mg/m² to about 5 mg/m², about 5 mg/m² to about 5.5 mg/m², about 5.5 mg/m² to about 6 mg/m², about 6 mg/m² to about 6.5 mg/m², about 6.5 mg/m² to about 7 mg/m², about 7 mg/m² to about 7.5 mg/m², about 7.5 mg/m² to about 8 mg/m², about 8 mg/m² to about 8.5 mg/m², about 8.5 mg/m² to about 9 mg/m², about 9 mg/m² to about 9.5 mg/m², about 9.5 mg/m² to about 10 mg/m², about 10 mg/m² to about 12 mg/m², about 12 mg/m² to about 14 mg/m², about 14 mg/m² to about 16 mg/m², about 16 mg/m² to about 18 mg/m², about 18 mg/m² to about 20 mg/m², about 20 mg/m² to about 25 mg/m², about 25 mg/m² to about 30 mg/m², about 30 mg/m² to about 35 mg/m², about 35 mg/m² to about 40 mg/m², about 40 mg/m² to about 45 mg/m², or about 45 mg/m² to about 50 mg/m². In certain embodiments, each dose of the formulation comprising ABDNAZ is administered to the patient by intravenous infusion providing ABDNAZ in an amount ranging from about 3 mg/m² to about 8 mg/m².

In more specific embodiments, each dose of the formulation comprising ABDNAZ is administered to the patient by intravenous infusion providing ABDNAZ in an amount of about 1.25 mg/m². In certain embodiments, each dose of the formulation comprising ABDNAZ is administered to the patient by intravenous infusion providing ABDNAZ in an amount of about 2.5 mg/m². In certain embodiments, each dose of the formulation comprising ABDNAZ is administered to the patient by intravenous infusion providing ABDNAZ in an amount of about 5 mg/m². In certain embodiments, each dose of the formulation comprising ABDNAZ is administered to the patient by intravenous infusion providing ABDNAZ in an amount of about 8.4 mg/m². In certain embodiments, each dose of the formulation comprising ABDNAZ is administered to the patient by intravenous infusion providing ABDNAZ in an amount of about 1 mg/m², about 1.5 mg/m², about 2 mg/m², about 2.5 mg/m², about 3 mg/m², about 3.5 mg/m², about 4 mg/m², about 4.5 mg/m², about 5 mg/m², about 5.5 mg/m², about 6 mg/m², about 6.5 mg/m², about 7 mg/m², about 7.5 mg/m², about 8 mg/m², about 8.5 mg/m², about 9 mg/m², about 9.5 mg/m², about 10 mg/m², about 12 mg/m², about 14 mg/m², about 16 mg/m², about 18 mg/m², about 20 mg/m², about 25 mg/m², about 30 mg/m², about 35 mg/m², about 40 mg/m², about 45 mg/m², or about 50 mg/m².

In yet other embodiments, each dose of the formulation comprising ABDNAZ is administered to the patient by intravenous infusion providing ABDNAZ in an amount of from about 0.1 mg to about 20 mg. In yet other embodiments, each dose of the formulation comprising ABDNAZ is administered to the patient by intravenous infusion providing ABDNAZ in an amount of from about 0.1 mg to about 10 mg. In yet other embodiments, each dose of the formulation comprising ABDNAZ is administered to the patient by intravenous infusion providing ABDNAZ in an amount of about 0.5 mg, 1.0 mg, 1.5 mg, 2.0 mg, 2.5 mg, 3.0 mg, 3.5 mg, or 4.0 mg.

Type of Brain Metastasis

The therapeutic method can be further characterized according to type of brain metastasis to be treated. For example, the brain metastasis can be characterized according to the type of primary tumor from which the brain metastasis results. In certain embodiments, the brain metastasis is a brain metastasis from a melanoma, lung cancer, breast cancer, colon cancer, kidney cancer, liver cancer, ovarian cancer, pancreatic cancer, prostate cancer, rectal cancer, stomach cancer, testicular cancer, uterine cancer, endometrial cancer, or esophageal cancer. In certain other embodiments, the brain metastasis is a brain metastasis from a melanoma, lung cancer, breast cancer, colon cancer, or kidney cancer. In yet other embodiments, the brain metastasis is from a melanoma.

Without limitation, exemplary cancers from which a brain metastasis may result include, for example, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, and uterine cancer. In yet other embodiments, the cancer is a vascularized tumor, squamous cell carcinoma, adenocarcinoma, small cell carcinoma, melanoma, glioma, neuroblastoma, sarcoma (e.g., an angiosarcoma or chondrosarcoma), larynx cancer, parotid cancer, bilary tract cancer, thyroid cancer, acral lentiginous melanoma, actinic keratoses, acute lymphocytic leukemia, acute myeloid leukemia, adenoid cystic carcinoma, adenomas, adenosarcoma, adenosquamous carcinoma, anal canal cancer, anal cancer, anorectum cancer, astrocytic tumor, bartholin gland carcinoma, basal cell carcinoma, biliary cancer, bone cancer, bone marrow cancer, bronchial cancer, bronchial gland carcinoma, carcinoid, cholangiocarcinoma, chondosarcoma, choriod plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intaepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VlPoma, vulva cancer, well differentiated carcinoma, or Wilms tumor.

Characterization of Treatment Effects

The therapeutic method may be further characterized according to the effect of the treatment, such as (i) a reduction in the size of at least one brain metastasis in the patient, and/or (ii) reduction in the number of brain metastases in the patient.

Accordingly, in certain embodiments, the therapeutic method is characterized by at least a 20% reduction in the size of at least one brain metastasis in the patient. In certain other embodiments, there is at least a 35% reduction in the size of at least one brain metastasis in the patient. In certain other embodiments, there is at least a 50% reduction in the size of at least one brain metastasis in the patient. In certain other embodiments, there is at least a 60%, 70%, 80% or 90% reduction in the size of at least one brain metastasis in the patient. In certain other embodiments, there is about a 5%-50%, 10%-50%, 20%-50%, 5%-75%, 10%-75%, 20%-75%, or 50%-90% reduction in the size of at least one brain metastasis in the patient.

In certain embodiments, there is at least a 20% reduction in the number of brain metastases in the patient. In certain other embodiments, there is at least a 35% reduction in the number of brain metastases in the patient. In yet other embodiments, there is at least a 50% reduction in the number of brain metastases in the patient. In certain other embodiments, there is at least a 60%, 70%, 80% or 90% reduction in the number of brain metastases in the patient. In certain other embodiments, there is about a 5%-50%, 10%-50%, 20%-50%, 5%-75%, 10%-75%, 20%-75%, or 50%-90% reduction in the number of brain metastases in the patient.

Patients for Treatment

The therapeutic method may be further characterized according to the patient to be treated. In certain embodiments, the patient is an adult human. In certain other embodiments, the patient is a pediatric human.

Form of ABDNAZ

In certain embodiments, the patient may be administered a pharmaceutically acceptable salt of ABDNAZ.

Additional Exemplary Features of the First, Second, and Third Methods

The first, second, and third methods may be further characterized by additional features, such as the timing for administering radiation therapy, as well as the timing for administering ABDNAZ.

Timing for Administering Radiation Therapy

As described generally above, the radiation therapy may be administered multiple times, such as multiple times over a defined period of time. Administration of radiation therapy on multiple consecutive days is contemplated to provide therapeutic benefits, such as superior efficacy. In certain embodiments, the brain metastasis is subjected to radiation therapy at a time in the range of 3 days to 5 days after administering the first dose of the therapeutically effective amount of a formulation comprising ABDNAZ. In certain embodiments, the brain metastasis is subjected to the first dose of radiation on the same day within 10 hours of administering the dose of a therapeutically effective amount of a formulation comprising ABDNAZ.

Timing for Administering ABDNAZ

A formulation comprising ABDNAZ may be administered multiple times, such as multiple times over a defined period of time. Further, coordination of the dosing schedule of the radiation therapy with that of the formulation comprising ABDNAZ is contemplated to provide therapeutic benefits, such as superior efficacy.

In certain embodiments, a dose of a therapeutically effective amount of a formulation comprising ABDNAZ is administered to the patient at a time in the range of 2 days to 4 days after subjecting the brain metastasis to the first dose of radiation therapy. In certain embodiments, a dose of a therapeutically effective amount of a formulation comprising ABDNAZ is administered to the patient on the third day after subjecting the brain metastasis to the first dose of radiation therapy.

In certain embodiments, a dose of a therapeutically effective amount of a formulation comprising ABDNAZ is administered to the patient at a time in the range of 6 days to 8 days after subjecting the brain metastasis to the first dose of radiation therapy. In certain embodiments, a dose of a therapeutically effective amount of a formulation comprising ABDNAZ is administered to the patient on the seventh day after subjecting the brain metastasis to the first dose of radiation therapy.

In certain embodiments, a dose of a therapeutically effective amount of a formulation comprising ABDNAZ is administered to the patient at a time in the range of 9 days to 11 days after subjecting the brain metastasis to the first dose of radiation therapy. In certain embodiments, a dose of a therapeutically effective amount of a formulation comprising ABDNAZ is administered to the patient on the tenth day after subjecting the brain metastasis to the first dose of radiation therapy.

In certain embodiments, a dose of a therapeutically effective amount of a formulation comprising ABDNAZ is administered to the patient at a time in the range of 3 days to 5 days prior to the first dose of radiation therapy. In certain embodiments, a dose of a therapeutically effective amount of a formulation comprising ABDNAZ is administered to the patient on the fourth day prior to the first dose of radiation therapy.

In certain embodiments, for a two-week period beginning on the day of the first dose of radiation therapy, any dose of a therapeutically effective amount of a formulation comprising ABDNAZ is administered to the patient on a day in which the brain metastasis is subjected to radiation therapy.

In certain embodiments, for a two-week period beginning on the day of the first dose of radiation therapy, the brain metastasis is subjected to a dose of radiation therapy within 10 hours after the dose of a therapeutically effective amount of a formulation comprising ABDNAZ has been administered to the patient. In certain embodiments, for a two-week period beginning on the day of the first dose of radiation therapy, the brain metastasis is subjected to a dose of radiation therapy within 6 hours after the dose of a therapeutically effective amount of a formulation comprising ABDNAZ has been administered to the patient.

In certain embodiments, for any dose of a formulation comprising ABDNAZ administered to the patient at a time that is later than two weeks after the first dose of radiation therapy, said dose of a formulation comprising ABDNAZ is administered to the patient on a once-weekly schedule no sooner than 7±1 days after administration of a prior dose of a formulation comprising ABDNAZ.

In certain embodiments, on 4±1 days prior to the first dose of radiation therapy, a dose of a therapeutically effective amount of a formulation comprising ABDNAZ is intravenously administering to the patient.

In certain embodiments, the method comprises the dosing schedule for a formulation comprising ABDNAZ as set for the below in Tables 1, 2, 3, or 4.

TABLE 1

| Step No. | Dosing Schedule |
|---|---|
| 1 | Administer one dose of a formulation comprising ABDNAZ and thereafter within 12 hours administer one dose of radiation therapy. |
| 2 | On the day that is 3 ± 1 days after Step 1, administer one dose of a formulation comprising ABDNAZ which is administered prior to administering one dose of radiation therapy on the same day. |
| 3 | On the day that is 7 ± 1 days after Step 1, administer one dose of a formulation comprising ABDNAZ and thereafter on the same day administer one dose of radiation therapy. |
| 4 | On the day that is 10 ± 1 days after Step 1, administer one dose of a formulation comprising ABDNAZ which is administered prior to administering one dose of radiation therapy on the same day. |

TABLE 2

| Step No. | Dosing Schedule |
|---|---|
| 1 | Administer one dose of a formulation comprising ABDNAZ and thereafter within 12 hours administer one dose of radiation therapy. |
| 2 | On four out of the next six days following Step 1, administer one dose of radiation therapy. |
| 3 | On the day that is 3 ± 1 days after Step 1, administer one dose of a formulation comprising ABDNAZ which is administered prior to administering one dose of radiation therapy on the same day. |
| 4 | On the day that is 7 ± 1 days after Step 1, administer one dose of a formulation comprising ABDNAZ and thereafter on the same day administer one dose of radiation therapy. |
| 5 | On four out of the next six days following Step 5, administer one dose of radiation therapy. |
| 6 | On the day that is 10 ± 1 days after Step 1, administer one dose of a formulation comprising ABDNAZ which is administered prior to administering one dose of radiation therapy on the same day. |

TABLE 3

| Step No. | Dosing Schedule |
|---|---|
| 1 | Administer one dose of a formulation comprising ABDNAZ and thereafter within 12 hours administer one dose of whole brain radiation therapy. |
| 2 | On four out of the next six days following Step 1, administer one dose of whole brain radiation therapy. |
| 3 | On the day that is 3 ± 1 days after Step 1, administer one dose of a formulation comprising ABDNAZ which is administered prior to administering one dose of whole brain radiation therapy on the same day. |
| 4 | On the day that is 7 ± 1 days after Step 1, administer one dose of a formulation comprising ABDNAZ and thereafter on the same day administer one dose of whole brain radiation therapy. |
| 5 | On four out of the next six days following Step 5, administer one dose of whole brain radiation therapy. |
| 6 | On the day that is 10 ± 1 days after Step 1, administer one dose of a formulation comprising ABDNAZ which is administered prior to administering one dose of whole brain radiation therapy on the same day. |

TABLE 4

| Step No. | Dosing Schedule |
|---|---|
| 1 | Administer one dose of a formulation comprising ABDNAZ and thereafter on the same day within 6 hours administer one 3 Gy dose of whole brain radiation therapy. |
| 2 | On four out of the next six days following Step 1, administer one 3 Gy dose of whole brain radiation therapy. |
| 3 | On the day that is 3 ± 1 days after Step 1, administer one dose of a formulation comprising ABDNAZ which is administered within 6 hours prior to administering one 3 Gy dose of whole brain radiation therapy on the same day. |
| 4 | On the day that is 7 ± 1 days after Step 1, administer one dose of a formulation comprising ABDNAZ and thereafter on the same day administer one 3 Gy dose of whole brain radiation therapy. |
| 5 | On four out of the next six days following Step 4, administer one 3 Gy dose of whole brain radiation therapy. |
| 6 | On the day that is 3 ± 1 days after Step 4, administer one dose of a formulation comprising ABDNAZ which is administered within 6 hours prior to administering one 3 Gy dose of whole brain radiation therapy on the same day. |

TABLE 5

| Step No | Dosing Schedule |
|---|---|
| 1 | Administer one dose of a formulation comprising ABDNAZ in an amount ranging from about 3 mg/m$^2$ to about 8 mg/m$^2$, and thereafter on the same day within 6 hours administer one dose of whole brain radiation therapy in an amount ranging from about 2 Gy to about 4 Gy of radiation. |
| 2 | On four out of the next six days following Step 1, administer one dose of whole brain radiation therapy in an amount ranging from about 2 Gy to about 4 Gy of radiation. |
| 3 | On the day that is 3 ± 1 days after Step 1, administer one dose of a formulation comprising ABDNAZ in an amount ranging from about 3 mg/m$^2$ to about 8 mg/m$^2$, which is administered within 6 hours prior to administering one dose of whole brain radiation therapy on the same day in an amount ranging from about 2 Gy to about 4 Gy of radiation. |
| 4 | On the day that is 7 ± 1 days after Step 1, administer one dose of a formulation comprising ABDNAZ in an amount ranging from about 3 mg/m$^2$ to about 8 mg/m$^2$, and thereafter on the same day administer one dose of whole brain radiation therapy in an amount ranging from about 2 Gy to about 4 Gy of radiation. |
| 5 | On four out of the next six days following Step 4, administer one dose of whole brain radiation therapy in an amount ranging from about 2 Gy to about 4 Gy of radiation. |

TABLE 5-continued

| Step No | Dosing Schedule |
|---|---|
| 6 | On the day that is 3 ± 1 days after Step 4, administer one dose of a formulation comprising ABDNAZ in an amount ranging from about 3 mg/m$^2$ to about 8 mg/m$^2$, which is administered within 6 hours prior to administering one dose of whole brain radiation therapy on the same day in an amount ranging from about 2 Gy to about 4 Gy of radiation. |

TABLE 6

| Step No | Dosing Schedule |
|---|---|
| 1 | Administer one dose of a formulation comprising ABDNAZ in an amount ranging from about 3 mg/m$^2$ to about 8 mg/m$^2$, and thereafter on the same day within 6 hours administer one dose of whole brain radiation therapy. |
| 2 | On four out of the next six days following Step 1, administer one 3 Gy dose of whole brain radiation therapy. |
| 3 | On the day that is 3 ± 1 days after Step 1, administer one dose of a formulation comprising ABDNAZ in an amount ranging from about 3 mg/m$^2$ to about 8 mg/m$^2$, which is administered within 6 hours prior to administering one 3 Gy dose of whole brain radiation therapy on the same day. |
| 4 | On the day that is 7 ± 1 days after Step 1, administer one dose of a formulation comprising ABDNAZ in an amount ranging from about 3 mg/m$^2$ to about 8 mg/m$^2$, and thereafter on the same day administer one 3 Gy dose of whole brain radiation therapy. |
| 5 | On four out of the next six days following Step 4, administer one 3 Gy dose of whole brain radiation therapy. |
| 6 | On the day that is 3 ± 1 days after Step 4, administer one dose of a formulation comprising ABDNAZ in an amount ranging from about 3 mg/m$^2$ to about 8 mg/m$^2$, which is administered within 6 hours prior to administering one 3 Gy dose of whole brain radiation therapy on the same day. |

Additional Exemplary Features of the Third, Fourth, and Fifth Methods

The third, fourth, and fifth methods may be further characterized by additional features, such as the timing for administering radiation therapy, as well as timing for administering ABDNAZ.

Timing for Administering Radiation Therapy

The radiation therapy may be administered multiple times, such as multiple times over a defined period of time. Administration of radiation therapy on multiple consecutive days is contemplated to provide therapeutic benefits, such as superior efficacy. In certain embodiments, the brain metastasis is subjected to radiation therapy at a time in the range of 3 days to 5 days after administering the first dose of the therapeutically effective amount of a formulation comprising ABDNAZ. In certain embodiments, the brain metastasis is subjected to radiation therapy on the fourth day after administering the first dose of the therapeutically effective amount of a formulation comprising ABDNAZ.

Timing for Administering ABDNAZ

A formulation comprising ABDNAZ may be administered multiple times, such as multiple times over a defined period of time. Further, coordination of the dosing schedule of the radiation therapy with that of the formulation comprising ABDNAZ is contemplated to provide therapeutic benefits, such as superior efficacy.

In certain embodiments, a second dose of a therapeutically effective amount of a formulation comprising ABDNAZ is administered to the patient within 10 hours prior to subjecting the brain metastasis to the first dose of radiation therapy. In certain embodiments, a second dose of a therapeutically effective amount of a formulation comprising ABDNAZ is administered to the patient within 6 hours prior to subjecting the brain metastasis to the first dose of radiation therapy.

In certain embodiments, a third dose of a therapeutically effective amount of a formulation comprising ABDNAZ is administered to the patient at a time in the range of 2 days to 4 days after administering the second dose of the therapeutically effective amount of a formulation comprising ABDNAZ. In certain embodiments, a third dose of a therapeutically effective amount of a formulation comprising ABDNAZ is administered to the patient on the third day after administering the second dose of the therapeutically effective amount of a formulation comprising ABDNAZ.

In certain embodiments, a fourth dose of a therapeutically effective amount of a formulation comprising ABDNAZ is administered to the patient at a time in the range of 6 days to 8 days after administering the second dose of the therapeutically effective amount of a formulation comprising ABDNAZ. In certain embodiments, a fourth dose of a therapeutically effective amount of a formulation comprising ABDNAZ is administered to the patient on the seventh day after administering the second dose of the therapeutically effective amount of a formulation comprising ABDNAZ.

In certain embodiments, a fifth dose of a therapeutically effective amount of a formulation comprising ABDNAZ is administered to the patient at a time in the range of 9 days to 11 days after administering the second dose of the therapeutically effective amount of a formulation comprising ABDNAZ. In certain embodiments, a fifth dose of a therapeutically effective amount of a formulation comprising ABDNAZ is administered to the patient on the tenth day after administering the second dose of the therapeutically effective amount of a formulation comprising ABDNAZ.

In certain embodiments, any subsequent dose (i.e., beyond the fifth dose) of a therapeutically effective amount of a formulation comprising ABDNAZ is administered to the patient on a once-weekly schedule no sooner than one week after administration of the fifth dose of the therapeutically effective amount of a formulation comprising ABDNAZ.

The therapeutic method can be further characterized according to the time at which the formulation comprising ABDNAZ is administered to the patient, such as by reference to the time at which the brain metastasis is subjected to radiation therapy. For example, in certain embodiments, the patient receives any second, third, fourth, or fifth dose of ABDNAZ within about 5 hours prior to subjecting the brain metastasis to radiation therapy. In certain embodiments, the patient receives any second, third, fourth, or fifth dose of ABDNAZ within about 4 hours prior to subjecting the brain metastasis to radiation therapy. In certain embodiments, the patient receives any second, third, fourth, or fifth dose of ABDNAZ within about 2 hours prior to subjecting the brain metastasis to radiation therapy. In certain embodiments, the patient receives any second, third, fourth, or fifth dose of ABDNAZ in about 3 hours to about 5 hours prior to subjecting the brain metastasis to radiation therapy.

In certain embodiments, the method comprises the dosing schedule for a formulation comprising ABDNAZ as set for the below in Tables 7-12.

TABLE 7

| Step No. | Dosing Schedule |
|---|---|
| 1 | Administer one dose of a formulation comprising ABDNAZ. |
| 2 | On the day that is 4 ± 2 days after Step 1, administer one dose of a formulation comprising ABDNAZ and thereafter on the same day administer one dose of radiation therapy. |
| 3 | On the day that is 3 ± 1 days after Step 2, administer one dose of a formulation comprising ABDNAZ which is administered prior to administering one dose of radiation therapy on the same day. |
| 4 | On the day that is 7 ± 1 days after Step 2, administer one dose of a formulation comprising ABDNAZ and thereafter on the same day administer one dose of radiation therapy. |
| 5 | On the day that is 3 ± 1 days after Step 4, administer one dose of a formulation comprising ABDNAZ which is administered prior to administering one dose of radiation therapy on the same day. |

TABLE 8

| Step No. | Dosing Schedule |
|---|---|
| 1 | Administer one dose of a formulation comprising ABDNAZ. |
| 2 | On the day that is 4 ± 2 days after Step 1, administer one dose of a formulation comprising ABDNAZ and thereafter on the same day administer one dose of radiation therapy. |
| 3 | On four out of the next six days following Step 2, administer one dose of radiation therapy. |
| 4 | On the day that is 3 ± 1 days after Step 2, administer one dose of a formulation comprising ABDNAZ which is administered prior to administering one dose of radiation therapy on the same day. |
| 5 | On the day that is 7 ± 1 days after Step 2, administer one dose of a formulation comprising ABDNAZ and thereafter on the same day administer one dose of radiation therapy. |
| 6 | On four out of the next six days following Step 5, administer one dose of radiation therapy. |
| 7 | On the day that is 3 ± 1 days after Step 5, administer one dose of a formulation comprising ABDNAZ which is administered prior to administering one dose of radiation therapy on the same day. |

TABLE 9

| Step No. | Dosing Schedule |
|---|---|
| 1 | Administer one dose of a formulation comprising ABDNAZ. |
| 2 | On the day that is 4 ± 1 days after Step 1, administer one dose of a formulation comprising ABDNAZ and thereafter on the same day administer one dose of whole brain radiation therapy. |
| 3 | On four out of the next six days following Step 2, administer one dose of whole brain radiation therapy. |
| 4 | On the day that is 3 ± 1 days after Step 2, administer one dose of a formulation comprising ABDNAZ which is administered prior to administering one dose of whole brain radiation therapy on the same day. |
| 5 | On the day that is 7 ± 1 days after Step 2, administer one dose of a formulation comprising ABDNAZ and thereafter on the same day administer one dose of whole brain radiation therapy. |
| 6 | On four out of the next six days following Step 5, administer one dose of whole brain radiation therapy. |
| 7 | On the day that is 3 ± 1 days after Step 5, administer one dose of a formulation comprising ABDNAZ which is administered prior to administering one dose of whole brain radiation therapy on the same day. |

TABLE 10

| Step No. | Dosing Schedule |
|---|---|
| 1 | Administer one dose of a formulation comprising ABDNAZ. |
| 2 | On the day that is 4 ± 2 days after Step 1, administer one dose of a formulation comprising ABDNAZ and thereafter on the same day administer one dose of radiation therapy. |
| 3 | On at least two out of the next six days following Step 2, administer one dose of radiation therapy. |
| 4 | On the day that is 3 ± 1 days after Step 2, administer one dose of a formulation comprising ABDNAZ which is administered prior to administering one dose of radiation therapy on the same day. |
| 5 | On the day that is 7 ± 1 days after Step 2, administer one dose of a formulation comprising ABDNAZ and thereafter on the same day administer one dose of radiation therapy. |
| 6 | On at least two out of the next six days following Step 5, administer one dose of radiation therapy. |
| 7 | On the day that is 3 ± 1 days after Step 5, administer one dose of a formulation comprising ABDNAZ which is administered prior to administering one dose of radiation therapy on the same day. |

TABLE 11

| Step No. | Dosing Schedule |
|---|---|
| 1 | Administer one dose of a formulation comprising ABDNAZ. |
| 2 | On the day that is 4 ± 2 days after Step 1, administer one dose of a formulation comprising ABDNAZ and thereafter on the same day administer one dose of radiation therapy. |
| 3 | On four out of the next six days following Step 2, administer one dose of radiation therapy. |
| 4 | On the day that is 3 ± 1 days after Step 2, administer one dose of a formulation comprising ABDNAZ which is administered prior to administering one dose of radiation therapy on the same day. |
| 5 | On the day that is 7 ± 1 days after Step 2, administer one dose of a formulation comprising ABDNAZ and thereafter on the same day administer one dose of radiation therapy. |
| 6 | On four out of the next six days following Step 5, administer one dose of radiation therapy. |
| 7 | On the day that is 3 ± 1 days after Step 5, administer one dose of a formulation comprising ABDNAZ which is administered prior to administering one dose of radiation therapy on the same day. |

TABLE 12

| Step No. | Dosing Schedule |
|---|---|
| 1 | Administer one dose of a formulation comprising ABDNAZ. |
| 2 | On the day that is 4 ± 2 days after Step 1, administer one dose of a formulation comprising ABDNAZ and thereafter on the same day administer one 3 Gy dose of whole brain radiation therapy. |
| 3 | On four out of the next six days following Step 2, administer one 3 Gy dose of whole brain radiation therapy. |
| 4 | On the day that is 3 ± 1 days after Step 2, administer one dose of a formulation comprising ABDNAZ which is administered prior to administering one 3 Gy dose of whole brain radiation therapy on the same day. |
| 5 | On the day that is 7 ± 1 days after Step 2, administer one dose of a formulation comprising ABDNAZ and thereafter on the same day administer one 3 Gy dose of whole brain radiation therapy. |
| 6 | On four out of the next six days following Step 5, administer one 3 Gy dose of whole brain radiation therapy. |
| 7 | On the day that is 3 ± 1 days after Step 5, administer one dose of a formulation comprising ABDNAZ which is administered prior to administering one 3 Gy dose of whole brain radiation therapy on the same day. |

Additional exemplary dosing procedures are described in Tables 13-15 below.

TABLE 13

| Step No. | Dosing Schedule |
|---|---|
| 1 | Administer one dose of a formulation comprising ABDNAZ in an amount ranging from about 3 mg/m² to about 8 mg/m². |
| 2 | On the day that is 4 ± 2 days after Step 1, administer one dose of a formulation comprising ABDNAZ in an amount ranging from about 3 mg/m² to about 8 mg/m² and thereafter on the same day administer one dose of whole brain radiation therapy. |
| 3 | On four out of the next six days following Step 2, administer one dose of whole brain radiation therapy. |
| 4 | On the day that is 3 ± 1 days after Step 2, administer one dose of a formulation comprising ABDNAZ in an amount ranging from about 3 mg/m² to about 8 mg/m² which is administered prior to administering one dose of whole brain radiation therapy on the same day. |
| 5 | On the day that is 7 ± 1 days after Step 2, administer one dose of a formulation comprising ABDNAZ in an amount ranging from about 3 mg/m² to about 8 mg/m² and thereafter on the same day administer one dose of whole brain radiation therapy. |
| 6 | On four out of the next six days following Step 5, administer one dose of whole brain radiation therapy. |
| 7 | On the day that is 3 ± 1 days after Step 5, administer one dose of a formulation comprising ABDNAZ in an amount ranging from about 3 mg/m² to about 8 mg/m² which is administered prior to administering one dose of whole brain radiation therapy on the same day. |

TABLE 14

| Step No | Dosing Shedule |
|---|---|
| 1 | Administer one dose of a formulation comprising ABDNAZ in an amount ranging from about 3 mg/m² to about 8 mg/m². |
| 2 | On the day that is 4 ± 2 days after Step 1, administer one dose of a formulation comprising ABDNAZ in an amount ranging from about 3 mg/m² to about 8 mg/m² and thereafter on the same day administer one dose of whole brain radiation therapy in an amount ranging from about 2 Gy to about 4 Gy of radiation. |
| 3 | On four out of the next six days following Step 2, administer one dose of whole brain radiation therapy in an amount ranging from about 2 Gy to about 4 Gy of radiation. |
| 4 | On the day that is 3 ± 1 days after Step 2, administer one dose of a formulation comprising ABDNAZ in an amount ranging from about 3 mg/m² to about 8 mg/m² which is administered prior to administering one dose of whole brain radiation therapy on the same day in an amount ranging from about 2 Gy to about 4 Gy of radiation. |
| 5 | On the day that is 7 ± 1 days after Step 2, administer one dose of a formulation comprising ABDNAZ in an amount ranging from about 3 mg/m² to about 8 mg/m² and thereafter on the same day administer one dose of whole brain radiation therapy in an amount ranging from about 2 Gy to about 4 Gy of radiation. |
| 6 | On four out of the next six days following Step 5, administer one dose of whole brain radiation therapy in an amount ranging from about 2 Gy to about 4 Gy of radiation. |
| 7 | On the day that is 3 ± 1 days after Step 5, administer one dose of a formulation comprising ABDNAZ in an amount ranging from about 3 mg/m² to about 8 mg/m² which is administered prior to administering one dose of whole brain radiation therapy on the same day in an amount ranging from about 2 Gy to about 4 Gy of radiation. |

TABLE 15

| Step No. | Dosing Schedule |
|---|---|
| 1 | Administer one dose of a formulation comprising ABDNAZ in an amount ranging from about 3 mg/m² to about 8 mg/m². |
| 2 | On the day that is 4 ± 2 days after Step 1, administer one dose of a formulation comprising ABDNAZ in an amount ranging from about 3 mg/m² to about 8 mg/m² and thereafter on the same day administer one 3 Gy dose of whole brain radiation therapy. |
| 3 | On four out of the next six days following Step 2, administer one 3 Gy dose of whole brain radiation therapy. |
| 4 | On the day that is 3 ± 1 days after Step 2, administer one dose of a formulation comprising ABDNAZ in an amount ranging from about 3 mg/m² to about 8 mg/m² which is administered prior to administering one 3 Gy dose of whole brain radiation therapy on the same day. |
| 5 | On the day that is 7 ± 1 days after Step 2, administer one dose of a formulation comprising ABDNAZ in an amount ranging from about 3 mg/m² to about 8 mg/m² and thereafter on the same day administer one 3 Gy dose of whole brain radiation therapy. |
| 6 | On four out of the next six days following Step 5, administer one 3 Gy dose of whole brain radiation therapy. |
| 7 | On the day that is 3 ± 1 days after Step 5, administer one dose of a formulation comprising ABDNAZ in an amount ranging from about 3 mg/m² to about 8 mg/m² which is administered prior to administering one 3 Gy dose of whole brain radiation therapy on the same day. |

Additional Exemplary Features of the Sixth Method

The sixth method may be further characterized by additional features, such as the dose of ABDNAZ, dose of temozolomide, dose of radiation therapy, and timing for administering various therapies.

Dose of ABDNAZ

In certain embodiments, each dose of the formulation comprising ABDNAZ is administered to the patient by intravenous infusion providing ABDNAZ in an amount of from about 0.1 mg to about 10 mg. In certain embodiments, each dose of the formulation comprising ABDNAZ is administered to the patient by intravenous infusion providing ABDNAZ in an amount of about 0.5 mg, 1.0 mg, 1.5 mg, 2.0 mg, 2.5 mg, 3.0 mg, 3.5 mg, or 4.0 mg. In certain embodiments, each dose of the formulation comprising ABDNAZ is administered to the patient by intravenous infusion providing ABDNAZ in an amount of about 0.5 mg. In certain embodiments, each dose of the formulation comprising ABDNAZ is administered to the patient by intravenous infusion providing ABDNAZ in an amount of about 2.0 mg. In certain embodiments, each dose of the formulation comprising ABDNAZ is administered to the patient by intravenous infusion providing ABDNAZ in an amount of about 4.0 mg.

Dose of Temozolomide

In certain embodiments, in steps (a) and (c) the temozolomide is administered at a dosage of about 75 mg/m². In certain embodiments, in steps (g) and (i) the temozolomide is administered at a dosage of about 150 mg/m².

Dose of Radiation Therapy

In certain embodiments, any daily dose of radiation therapy is from about 1 Gy to about 3 Gy of radiation.

Timing for Administering Various Therapies

In certain embodiments, beginning on day 15 following administration of the first dose of radiation therapy, the patient does not receive ABDNAZ, radiation therapy, or any other anti-cancer agent for a duration of seven days. In certain embodiments, beginning on day 29 following administration of the first dose of radiation therapy, the patient does not receive ABDNAZ, radiation therapy, or any other anti-cancer agent for a duration of seven days. In certain embodiments, in step (b) the radiation therapy is administered once per day for four days within the 6 day period, and in step (e) the radiation therapy is administered once per day for five days within the 7 day period. In certain embodiments, the radiation therapy provides from about 10 Gy to about 20 Gy of radiation each week for a period of two weeks beginning on the day on which the brain metastasis is subjected to the first dose of radiation therapy.

In certain embodiments, the method comprises (or in the alternative, consists of) the dosing schedule set forth in Table 16.

TABLE 16

| Step No. | Dosing Schedule |
|---|---|
| 1 | intravenously administering to the patient in need thereof a dose of a therapeutically effective amount of a formulation comprising ABDNAZ, and thereafter on the same day orally administering temozolomide at a dosage of 75 mg/m$^2$ to the patient and subjecting the brain metastasis to a first dose of radiation therapy, wherein the radiation therapy provides from about 2 Gy to about 3 Gy of radiation |
| 2 | beginning on the day following administration of a first dose of radiation therapy, subjecting the brain metastasis to radiation therapy once per day for four days at a daily dosage of from about 2 Gy to about 3 Gy of radiation within a 6 day period |
| 3 | beginning on the day following administration of a first dose of radiation therapy, orally administering temozolomide at a daily dosage of 75 mg/m$^2$ to the patient once per day for 13 consecutive days |
| 4 | on day 7 ± 1 following administration of the first dose of radiation therapy, intravenously administering to the patient a dose of a therapeutically effective amount of a formulation comprising ABDNAZ prior to administration of temozolomide and radiation therapy on the same day |
| 5 | beginning on day 7 ± 1 following administration of the first dose of radiation therapy, subjecting the brain metastasis to radiation therapy once per day for five days at a daily dosage of from about 2 Gy to about 3 Gy of radiation within a 7 day period |
| 7 | on day 21 ± 1 following administration of the first dose of radiation therapy, intravenously administering to the patient a dose of a therapeutically effective amount of a formulation comprising ABDNAZ |
| 8 | on day 21 ± 1 following administration of the first dose of radiation therapy, orally administering temozolomide at a daily dosage of 150 mg/m$^2$ to the patient once per day for 7 consecutive days |
| 9 | on day 36 ± 1 following administration of the first dose of radiation therapy, intravenously administering to the patient a dose of a therapeutically effective amount of a formulation comprising ABDNAZ |
| 10 | on day 36 ± 1 following administration of the first dose of radiation therapy, orally administering temozolomide at a daily dosage of 150 mg/m$^2$ to the patient once per day for 7 consecutive days; |

IV. Pharmaceutical Compositions

The invention provides pharmaceutical compositions comprising ABDNAZ. The pharmaceutical compositions preferably comprise a therapeutically-effective amount of ABDNAZ, formulated together with one or more pharmaceutically acceptable carriers (additives) and/or diluents. As described in detail below, the pharmaceutical compositions of the present invention may be specially formulated for administration in liquid form, including those adapted for the following: (1) oral administration, for example, drenches (aqueous or non-aqueous solutions or suspensions); and (2) parenteral administration by, for example, subcutaneous, intramuscular, intravenous or epidural injection as, for example, a sterile solution or suspension, or sustained-release formulation.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The preparations of the present invention may be given, for example, orally or parenterally. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The description above describes multiple aspects and embodiments of the invention. The patent application specifically contemplates all combinations and permutations of the aspects and embodiments.

V. Kits for Use in Medical Applications

Another aspect of the invention provides a kit for treating a brain metastasis. The kit comprises: (i) a formulation comprising ABDNAZ, and (ii) instructions for treating a brain metastasis according to procedures described herein, such as (a) administering to the patient in need thereof a dose of a therapeutically effective amount of a formulation comprising ABDNAZ, and thereafter (b) subjecting the brain metastasis to a first dose of radiation therapy (e.g., within 24 hours after completing step (a)), wherein the radiation therapy provides from about 1 Gy to about 6 Gy of radiation.

VI. Definitions

To facilitate an understanding of the present invention, a number of terms and phrases are defined below.

The terms "a" and "an" as used herein mean "one or more" and include the plural unless the context is inappropriate.

As used herein, the term "patient" refers to organisms to be treated by the methods of the present invention. Such organisms are preferably mammals (e.g., murines, simians, equines, bovines, porcines, canines, felines, and the like), and more preferably humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route.

As used herein, the term "treating" includes any effect, e.g., lessening, reducing, modulating, ameliorating or eliminating, that results in the improvement of the condition, disease, disorder, and the like, or ameliorating a symptom thereof.

As used herein, the terms "alleviate" and "alleviating" refer to reducing the severity of the condition, such as reducing the severity by, for example, at least 10%, 20%, 30%, 40%, 50%, 60%, 70%, 80%, 90%, or 95%.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, for example, Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as Nat $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "about" as used herein when referring to a measurable value (e.g., weight, time, and dose) is meant to encompass variations, such as ±10%, ±5%, ±1%, or ±0.1% of the specified value.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

EXAMPLES

The invention now being generally described, will be more readily understood by reference to the following examples, which are included merely for purposes of illustration of certain aspects and embodiments of the present invention, and are not intended to limit the invention.

Example 1—Treatment of Human Patients Suffering from Brain Metastases

Two human patients suffering from brain metastases were treated according to the protocol described in Part I below using ABDNAZ in combination with whole brain radiation therapy. Results presented in Part II below describe the significant reduction in brain metastasis mass observed in the first patient due to the combination therapy and significant reduction in the number of brain metastases in the second patient to the combination therapy.

Part I—Procedure

ABDNAZ and whole brain radiation therapy were administered to the patient according to the dosing schedule provided in Table 17. ABDNAZ was administered intravenously in a formulation containing ABDNAZ, polyethylene glycol having a number-average molecular weight of 400 g/mol (PEG-400), water for injection, and N,N-dimethylacetamide. A single dosage of ABDNAZ was 5 mg/m². During radiation therapy, (i) subjects were treated in the supine position, (ii) adequate immobilization and reproducibility of position was ensured using thermoplastic mask, (iii) the target volume included the whole brain, per the treating radiation oncologist, (iv) the lens of the eye was excluded from the beam using shielding or by beam collimation, (v) the dose of radiation is specified at central axis at mid-plane, (vi) whole brain radiotherapy was delivered with a daily fraction size of 3.0 Gy per fraction given 5 days a week for a total dose of 30 Gy, and (vii) radiation therapy was delivered using photon beam energies of 6 MV and an opposed lateral technique, where all fields are treated during each treatment session.

TABLE 17

| Step No. | Medical Procedure |
|---|---|
| 1 | Administer one dose of ABDNAZ. |
| 2 | On the day that is 4 ± 2 days after Step 1, administer one dose of ABDNAZ and thereafter on the same day administer one 3 Gy dose of whole brain radiation therapy. |
| 3 | On four out of the next six days following step 2, administer one 3 Gy dose of whole brain radiation therapy. |
| 4 | On the day that is 3 ± 1 days after Step 2, administer one dose of ABDNAZ which is administered prior to administering one 3 Gy dose of whole brain radiation therapy on the same day. |
| 5 | On the day that is 7 ± 1 days after Step 2, administer one dose of ABDNAZ and thereafter on the same day administer one 3 Gy dose of whole brain radiation therapy. |
| 6 | On four out of the next six days following step 5, administer one 3 Gy dose of whole brain radiation therapy. |
| 7 | On the day that is 3 ± 1 days after Step 5, administer one dose of ABDNAZ which is administered prior to administering one 3 Gy dose of whole brain radiation therapy on the same day. |

Part II—Results

Results observed in a first human patient and second human patient that received the ABDNAZ/whole brain radiation therapy are provided below.

First Patient

A 62-year-old white male was initially diagnosed with cutaneous melanoma of the left arm for which he underwent wide local excision and sentinel lymph node biopsy, demonstrating melanoma (nodular type, Breslow depth 3.5 mm without ulceration) and 1 of 5 lymph nodes positive. Completion axillary lymph node dissection revealed no further disease. He presented 3 years later with biopsy proven recurrence in the left axilla. Staging work-up revealed no other sites of disease. He underwent reoperative axillary lymph node dissection, which demonstrated melanoma involving the subcutaneous tissue (measuring 2 cm in greatest diameter), and seven lymph nodes negative for neoplasm. The patient underwent adjuvant axillary radiation, and did well until 5 months later when he developed new-onset cough with a CT chest revealing new pulmonary nodules measuring up to 1.9 cm, confirmed by biopsy to be melanoma, as well as soft tissue nodules in the anterior abdomen.

Soon thereafter the patient noted decreased visual acuity and central and right-sided visual field deficit. Brain MRI revealed the presence of a 2.2×2.6×2.6 cm mass in the left occipital lobe and a 3.3×2.7×2.2 cm mass in the right occipital lobe, as well as 3 other supratentorial lesions. All lesions were hemorrhagic with surrounding vasogenic edema. Dexamethasone 4 mg TID was started without improvement in symptoms.

Next, the patient began receiving treatment according to the protocol described in Part I above for administration of ABDNAZ and whole brain radiation therapy. Twenty-four hours after receiving the first dose of ABDNAZ, dynamic contrast-enhanced brain MRI (DCE-MRI) revealed a decrease in $k^{trans}$ in 4 of 5 lesions, suggesting a reduction in vessel leakiness after exposure to the drug. Within 48 hours of receiving the first dose of radiation therapy, the patient's visual symptoms began to improve.

ABDNAZ was well-tolerated with mild, transient infusion site pain, and without any signs of systemic or neurologic toxicity. By the end of treatment, the patient reported improved visual symptoms with near resolution of visual field-deficit, and dexamethasone was tapered following completion of WRBT.

Four weeks after the completion of treatment using ABDNAZ and WBRT, a contrasted brain MRI confirmed a decrease in the size of the largest right and left occipital masses, and evolving hemorrhagic change in the other 3 lesions consistent with resolving hemorrhage. The patient reported full physical function with no impairment of activities of daily living, as reported by the Barthel ADL Index, which was unchanged from baseline. Four months after completion of treatment using ABDNAZ and WBRT, continued response was seen in all evaluable lesions (left occipital lobe lesion now measuring 0.9×0.6×1.0 cm, and right occipital lobe lesion measuring 2.3×2.2×1.5 cm), in addition to a decrease in associated edema of all lesions that were also improved compared to prior. A new, 5 mm lesion was discovered at 4 months after the completion of treatment using ABDNAZ and WBRT, possibly from seeding due to persistent systemic disease.

Second Patient

The second patient was a 40-year-old white male initially diagnosed with a melanoma of the upper back 5 years ago (Clark level IV, Breslow depth 1.5 mm) arising from a compound nevus. The patient underwent wide local excision and sentinel lymph node biopsy with axillary dissection of the right and left axilla, revealing 1 of 21 lymph nodes and 1 of 18 lymph nodes involved, respectively. He elected to undergo surveillance, and remained disease free until 5 years later when he developed progressive right arm pain. Restaging confirmed recurrent metastases involving the superior mediastinum, multiple subcutaneous sites, retroperitoneal adenopathy and at least 18 new brain metastases, most measuring 2-3 mm with the largest, partially hemorrhagic lesion measuring 1.7 cm.

The patient began receiving treatment according to the protocol described in Part I above for administration of ABDNAZ and whole brain radiation therapy. Twenty-four hours after first administration of ABDNAZ, a slight reduction in $k^{trans}$ was noted in the largest evaluable lesion. Sub-centimeter lesions could not be quantitatively evaluated with DCE-MRI due to their small size. The patient had no significant infusion site pain during treatment.

At one-month after the end of treatment using ABDNAZ and whole brain radiation therapy, the patient reported full physical function and ability to perform activities of daily living (as measuring by the Barthel ADL index), which was unchanged from baseline. Serial re-imaging revealed response in all 18 visualized lesions with complete disappearance of 3 sub-centimeter metastases 3 months after the end of treatment using ABDNAZ and whole brain radiation therapy.

Example 2—Treatment of Additional Human Patients Suffering from Brain Metastases Thirteen human patients suffering from brain metastases were treated according to the protocol described in Part I below using ABDNAZ in combination with whole brain radiation therapy. Results are presented in Part II below.

Part I—Procedure

ABDNAZ and whole brain radiation therapy were administered to the patient according to the dosing schedule provided in Table 18. ABDNAZ was administered intravenously at a dosage in the range of 1.25 mg/m² to 8.4 mg/m². During radiation therapy, (i) subjects were treated in the supine position, (ii) adequate immobilization and reproducibility of position was ensured using thermoplastic mask, (iii) the target volume included the whole brain, per the treating radiation oncologist, (iv) the lens of the eye was excluded from the beam using shielding or by beam collimation, (v) the dose of radiation is specified at central axis at mid-plane, (vi) whole brain radiotherapy was delivered with a daily fraction size of 3.0 Gy per fraction given 5 days a week for a total dose of 30 Gy, and (vii) radiation therapy was delivered using photon beam energies of 6 MV and an opposed lateral technique, where all fields are treated during each treatment session.

TABLE 18

| Step No. | Medical Procedure |
|---|---|
| 1 | Administer one dose of a formulation comprising ABDNAZ. |
| 2 | On the day that is 4 ± 2 days after Step 1, administer one dose of a formulation comprising ABDNAZ and thereafter on the same day administer one 3 Gy dose of whole brain radiation therapy. |
| 3 | On four out of the next six days following Step 2, administer one 3Gy dose of whole brain radiation therapy. |
| 4 | On the day that is 3 ± 1 days after Step 2, administer one dose of a formulation comprising ABDNAZ which is administered prior to administering one dose of whole brain radiation therapy on the same day. |
| 5 | On the day that is 7 ± 1 days after Step 2, administer one dose of a formulation comprising ABDNAZ and thereafter on the same day administer one 3 Gy dose of whole brain radiation therapy. |
| 6 | On four out of the next six days following Step 5, administer one 3 Gy dose of whole brain radiation therapy. |
| 7 | On the day that is 3 ± 1 days after Step 5, administer one dose of a formulation comprising ABDNAZ which is administered prior to administering one dose of whole brain radiation therapy on the same day. |

Part II—Results

No adverse events were observed due to administration of the ABDNAZ and radiation therapy. Approximately 50% of patients were observed to have at least the following measured improvement in their brain metastases: (i) a decrease of at least 30% in the sum of the longest diameters of target lesions compared to baseline sum longest diameters and (ii) an absolute decrease of at least 5 mm in at least one target lesion.

Example 3—Evaluation of Impact of Time Between Administration of ABDNAZ and Radiation Therapy on Tumor Growth Delay The impact of the time interval between administration of ABDNAZ and radiation therapy on tumor growth delay was evaluated in mice having a SCC VII tumor. Experimental procedures and results are described below.

Part I—Procedure

Mice having a SCC VII tumor were treated with radiation therapy and ABDNAZ, where the length of time between administration of radiation therapy and ABDNAZ was varied. Radiation therapy was administered as a single local dose of 7 Gy of radiation. ABDNAZ was dosed in 5 groups of mice at 15 mg/kg IP as a single dose at one of the following time points: 24 hours prior to radiation therapy, 2 hours prior to radiation therapy, concurrent with radiation therapy, 2 hours after radiation therapy, or 24 hours after radiation therapy.

Part II—Results

Results showing impact of the combination therapy on tumor growth delay are provided in FIG. 1, where negative hours refers to the amount of time between first administering ABDNAZ and later administering radiation therapy. Maximum tumor growth delay occurred when ABDNAZ was administered minutes before or concomitant with radiation therapy.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A method of treating a brain metastasis in a patient, the method comprising:
   (a) administering to the patient a dose of a therapeutically effective amount of a formulation comprising ABDNAZ; and thereafter
   (b) subjecting the brain metastasis to a first dose of radiation therapy within 24 hours after completing step (a); wherein the first dose of the radiation therapy provides from about 1 Gy to about 6 Gy of radiation; to thereby treat the brain metastasis in the patient.

2. The method of claim 1, wherein the brain metastasis is subjected to radiation therapy once per day for at least 4 days within a 6 day period following the first dose of radiation therapy.

3. The method of claim 2, wherein starting on the seventh day following the first dose of radiation therapy, the brain metastasis is subjected to radiation therapy once per day for at least 5 days within a 7 day period.

4. The method of claim 3, wherein a dose of a therapeutically effective amount of a formulation comprising ABDNAZ is administered to the patient at a time in the range of 6 days to 8 days after subjecting the brain metastasis to the first dose of radiation therapy.

5. The method of claim 3, wherein a dose of a therapeutically effective amount of a formulation comprising ABDNAZ is administered to the patient on the seventh day after subjecting the brain metastasis to the first dose of radiation therapy.

6. The method of claim 4, wherein for a two-week period beginning on the day of the first dose of radiation therapy, any dose of a therapeutically effective amount of a formulation comprising ABDNAZ is administered to the patient on a day in which the brain metastasis is subjected to radiation therapy.

7. The method of claim 4, wherein for a two-week period beginning on the day of the first dose of radiation therapy, the brain metastasis is subjected to a dose of radiation therapy within 6 hours after the dose of a therapeutically effective amount of a formulation comprising ABDNAZ has been administered to the patient.

8. The method of claim 4, wherein for any dose of a formulation comprising ABDNAZ administered to the patient at a time that is later than two weeks after the first dose of radiation therapy, said any dose of a formulation comprising ABDNAZ is administered to the patient on a once-weekly schedule no sooner than 7±1 days after administration of a prior dose of a formulation comprising ABDNAZ.

9. The method of claim 8, wherein each dose of radiation therapy provides about 3 Gy of radiation.

10. The method of claim 8, wherein each of (i) the first dose of radiation therapy and the radiation therapy once per day for at least 4 days within a 6 day period following the first dose of radiation therapy, and (ii) the radiation therapy once per day for at least 5 days within a 7 day period starting on the seventh day following the first dose of radiation therapy provides from about 10 Gy to about 20 Gy of radiation.

11. The method of claim 10, wherein each dose of the formulation comprising ABDNAZ is administered to the patient by intravenous infusion providing ABDNAZ in an amount ranging from about 1 mg/m$^2$ to about 10 mg/m$^2$.

12. The method of claim 10, wherein each dose of the formulation comprising ABDNAZ is administered to the patient by intravenous infusion providing ABDNAZ in an amount of from about 0.1 mg to about 10 mg.

13. The method of claim 8, further comprising administering an additional anti-cancer agent.

14. The method of claim 13, wherein the additional anti-cancer agent is temozolomide, cisplatin, carboplatin, trastuzumab, or sunitinib.

15. The method of claim 13, wherein the additional anti-cancer agent is temozolomide.

16. The method of claim 15, wherein for any day in which temozolomide is administered to the patient, the temozolomide is administered orally at a dosage of from about 75 mg/m$^2$ to about 150 mg/m$^2$.

17. A method of treating a brain metastasis in a patient, the method comprising:
   (a) intravenously administering to the patient a dose of a therapeutically effective amount of a formulation comprising ABDNAZ, and thereafter on the same day subjecting the brain metastasis to a first dose of radiation therapy, wherein the radiation therapy provides from about 1 Gy to about 4 Gy of radiation;

(b) beginning on the day following administration of a first dose of radiation therapy, subjecting the brain metastasis to radiation therapy once per day for four consecutive days;

(c) on day 3±1 following administration of the first dose of radiation therapy, intravenously administering to the patient a dose of a therapeutically effective amount of a formulation comprising ABDNAZ prior to administration of radiation therapy on the same day;

(d) beginning on day 7±1 following administration of the first dose of radiation therapy, subjecting the brain metastasis to radiation therapy once per day for five consecutive days;

(e) on day 7±1 following administration of the first dose of radiation therapy, intravenously administering to the patient a dose of a therapeutically effective amount of a formulation comprising ABDNAZ prior to administration of radiation therapy on the same day; and (f) on day 10±1 following administration of the first dose of radiation therapy, intravenously administering to the patient a dose of a therapeutically effective amount of a formulation comprising ABDNAZ prior to administration of radiation therapy on the same day;

to thereby treat the brain metastasis in the patient.

18. A method of treating a brain metastasis in a patient, the method comprising:

(a) intravenously administering to the patient a dose of a therapeutically effective amount of a formulation comprising ABDNAZ, and thereafter on the same day orally administering temozolomide to the patient and subjecting the brain metastasis to a first dose of radiation therapy, wherein the radiation therapy provides from about 1 Gy to about 4 Gy of radiation;

(b) beginning on the day following administration of a first dose of radiation therapy, subjecting the brain metastasis to radiation therapy once per day for at least four days within a 6 day period;

(c) beginning on the day following administration of a first dose of radiation therapy, orally administering temozolomide to the patient once per day for 13 consecutive days;

(d) on day 7±1 following administration of the first dose of radiation therapy, intravenously administering to the patient a dose of a therapeutically effective amount of a formulation comprising ABDNAZ prior to administration of temozolomide and radiation therapy on the same day;

(e) beginning on day 7±1 following administration of the first dose of radiation therapy, subjecting the brain metastasis to radiation therapy once per day for at least five days within a 7 day period;

(f) on day 21±1 following administration of the first dose of radiation therapy, intravenously administering to the patient a dose of a therapeutically effective amount of a formulation comprising ABDNAZ;

(g) on day 21±1 following administration of the first dose of radiation therapy, orally administering temozolomide to the patient once per day for 7 consecutive days;

(h) on day 36±1 following administration of the first dose of radiation therapy, intravenously administering to the patient a dose of a therapeutically effective amount of a formulation comprising ABDNAZ; and (i) on day 36±1 following administration of the first dose of radiation therapy, orally administering temozolomide to the patient once per day for 7 consecutive days;

to thereby treat the brain metastasis in the patient.

19. The method of claim 18, wherein each dose of the formulation comprising ABDNAZ is administered to the patient by intravenous infusion providing ABDNAZ in an amount of from about 0.1 mg to about 10 mg.

20. The method of claim 18, wherein each dose of the formulation comprising ABDNAZ is administered to the patient by intravenous infusion providing ABDNAZ in an amount of about 0.5 mg, 1.0 mg, 1.5 mg, 2.0 mg, 2.5 mg, 3.0 mg, 3.5 mg, or 4.0 mg.

21. The method of claim 18, wherein in steps (a) and (c) the temozolomide is administered at a dosage of about 75 mg/m$^2$.

22. The method of claim 18, wherein any daily dose of radiation therapy is from about 1 Gy to about 3 Gy of radiation.

23. The method of claim 18, wherein in step (b) the radiation therapy is administered once per day for four days within the 6 day period, and in step (e) the radiation therapy is administered once per day for five days within the 7 day period.

24. The method of claim 18, wherein the radiation provides from about 10 Gy to about 20 Gy of radiation-each week for a period of two weeks beginning on the day on which the brain metastasis is subjected to the first dose of radiation therapy.

25. The method of claim 18, wherein the brain metastasis is a brain metastasis from a melanoma, lung cancer, breast cancer, colon cancer, kidney cancer, liver cancer, ovarian cancer, pancreatic cancer, prostate cancer, rectal cancer, stomach cancer, testicular cancer, uterine cancer, endometrial cancer, or esophageal cancer.

26. The method of claim 18, wherein the brain metastasis is a brain metastasis from a melanoma, lung cancer, breast cancer, colon cancer, or kidney cancer.

27. The method of claim 18, wherein the brain metastasis is from a melanoma.

28. The method of claim 18, wherein the patient is an adult human.

29. The method of claim 18, wherein there is at least a 35% reduction in the size of the brain metastasis in the patient.

30. The method of claim 18, wherein the patient has a number of brain metastases and there is at least a 50% reduction in the number of brain metastases in the patient.

* * * * *